(12) United States Patent
Schraga

(10) Patent No.: US 8,961,470 B2
(45) Date of Patent: Feb. 24, 2015

(54) PEN NEEDLE WITH SAFETY SHIELD SYSTEM

(76) Inventor: Steven Schraga, Surfside, FL (US)

( * ) Notice: Subject to any disclaimer, the term of this patent is extended or adjusted under 35 U.S.C. 154(b) by 126 days.

(21) Appl. No.: 13/398,173

(22) Filed: Feb. 16, 2012

(65) Prior Publication Data

US 2012/0226233 A1  Sep. 6, 2012

Related U.S. Application Data

(60) Provisional application No. 61/443,958, filed on Feb. 17, 2011.

(51) Int. Cl.
*A61M 5/32* (2006.01)
*A61M 5/50* (2006.01)

(52) U.S. Cl.
CPC ........................... *A61M 5/50* (2013.01)
USPC ................... 604/198; 604/110; 604/192

(58) Field of Classification Search
USPC ................. 604/110, 111, 181, 192, 198
See application file for complete search history.

(56) References Cited

U.S. PATENT DOCUMENTS

| | | | |
|---|---|---|---|
| 4,894,055 A | 1/1990 | Sudnak | |
| 4,909,792 A | 3/1990 | Norelli | |
| 4,973,318 A | 11/1990 | Holm et al. | |
| 5,242,401 A | 9/1993 | Colsky | |
| 5,242,416 A | 9/1993 | Hutson | |
| 5,389,085 A | 2/1995 | D'Alessio et al. | |
| 5,419,773 A | 5/1995 | Rupp | |
| 5,454,828 A | 10/1995 | Schraga | |
| 5,591,138 A | 1/1997 | Vaillancourt | |
| 5,593,387 A | 1/1997 | Rupp | |
| 5,611,786 A | 3/1997 | Kirchhofer et al. | |
| 5,980,488 A | 11/1999 | Thorne | |
| 6,117,108 A | 9/2000 | Woehr et al. | |
| D445,602 S | 7/2001 | Tonon | |
| 6,287,278 B1 | 9/2001 | Woehr et al. | |
| 6,379,333 B1 | 4/2002 | Brimhall et al. | |
| 6,391,003 B1 | 5/2002 | Lesch, Jr. | |
| 6,460,234 B1 | 10/2002 | Gianchandani | |
| 6,470,754 B1 | 10/2002 | Gianchandani | |
| 6,616,630 B1 | 9/2003 | Woehr et al. | |
| 6,652,490 B2 | 11/2003 | Howell | |
| 6,749,588 B1 | 6/2004 | Howell et al. | |
| 6,855,129 B2 | 2/2005 | Jensen et al. | |
| 7,125,397 B2 | 10/2006 | Woehr et al. | |
| 7,214,211 B2 | 5/2007 | Woehr et al. | |

(Continued)

FOREIGN PATENT DOCUMENTS

| | | |
|---|---|---|
| EP | 2 090 326 | 8/2009 |
| WO | 99/08742 | 2/1999 |

(Continued)

*Primary Examiner* — Laura Bouchelle
(74) *Attorney, Agent, or Firm* — Greenblum & Bernstein, P.L.C.

(57) ABSTRACT

A needle tip for an injection device includes a body having a front portion, a back portion configured to be removably connected to the pre-loaded injection device, and a wall separating the front and back portions. A hollow needle has a first piercing portion projecting back from the separating wall and a second piercing portion projecting forward from the separating wall. A safety shield that is axially movable relative to the body at least between an initial position, a retracted position, and a post use locking position. This Abstract is not intended to define the invention disclosed in the specification, nor intended to limit the scope of the invention in any way.

11 Claims, 43 Drawing Sheets

(56) References Cited

U.S. PATENT DOCUMENTS

| | | |
|---|---|---|
| 7,264,613 B2 | 9/2007 | Woehr et al. |
| 7,462,168 B2 * | 12/2008 | Stonehouse et al. .......... 604/198 |
| 7,540,858 B2 | 6/2009 | DiBiasi |
| 7,553,293 B2 | 6/2009 | Jensen et al. |
| 7,871,397 B2 | 1/2011 | Schraga |
| 2002/0004648 A1 | 1/2002 | Larsen et al. |
| 2002/0133122 A1 | 9/2002 | Giambattista et al. |
| 2003/0014018 A1 | 1/2003 | Giambattista et al. |
| 2003/0105431 A1 | 6/2003 | Howell |
| 2003/0195471 A1 | 10/2003 | Woehr et al. |
| 2004/0116856 A1 | 6/2004 | Woehr et al. |
| 2004/0186434 A1 | 9/2004 | Harding et al. |
| 2004/0204681 A1 | 10/2004 | Thoresen et al. |
| 2004/0236284 A1 | 11/2004 | Hoste et al. |
| 2004/0236288 A1 | 11/2004 | Howell et al. |
| 2005/0004532 A1 | 1/2005 | Woehr et al. |
| 2005/0038392 A1 | 2/2005 | DeSalvo |
| 2005/0080378 A1 | 4/2005 | Cindrich et al. |
| 2005/0107748 A1 | 5/2005 | Thorne et al. |
| 2005/0171485 A1 * | 8/2005 | Larsen et al. ................. 604/198 |
| 2005/0277881 A1 | 12/2005 | Sibbitt |
| 2005/0277895 A1 | 12/2005 | Giambattista et al. |
| 2005/0283115 A1 | 12/2005 | Giambattista et al. |
| 2006/0229652 A1 | 10/2006 | Iio et al. |
| 2006/0264828 A1 | 11/2006 | Woehr et al. |
| 2007/0049868 A1 | 3/2007 | Woehr et al. |
| 2007/0083159 A1 | 4/2007 | Woehr et al. |
| 2007/0100297 A1 | 5/2007 | Woehr et al. |
| 2007/0129689 A1 | 6/2007 | Woehr et al. |
| 2007/0203458 A1 | 8/2007 | Tsubota |
| 2008/0108951 A1 | 5/2008 | Jerde et al. |
| 2008/0154192 A1 | 6/2008 | Schraga |
| 2008/0177237 A1 | 7/2008 | Stonehouse et al. |
| 2008/0177238 A1 | 7/2008 | Follman et al. |
| 2009/0069753 A1 | 3/2009 | Ruan et al. |
| 2009/0254042 A1 * | 10/2009 | Gratwohl et al. ............. 604/198 |
| 2010/0292654 A1 | 11/2010 | Schraga |
| 2011/0022001 A1 | 1/2011 | Wei |
| 2011/0077615 A1 | 3/2011 | Schraga |
| 2011/0106016 A1 | 5/2011 | Wei |
| 2011/0118667 A1 | 5/2011 | Zaiken et al. |
| 2011/0160675 A1 | 6/2011 | Ruan et al. |
| 2011/0288526 A1 | 11/2011 | Wei |

FOREIGN PATENT DOCUMENTS

| | | |
|---|---|---|
| WO | 00/69501 | 11/2000 |
| WO | WO 2008/077706 | 7/2008 |

* cited by examiner

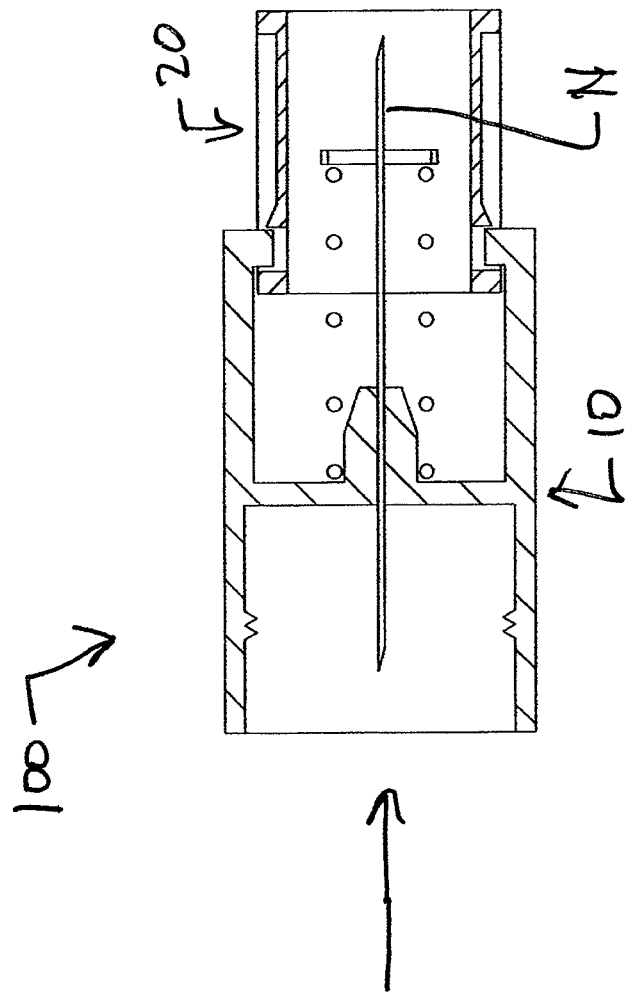
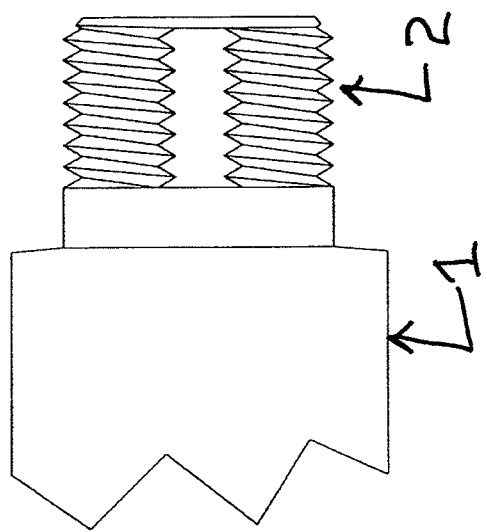
Fig. 5

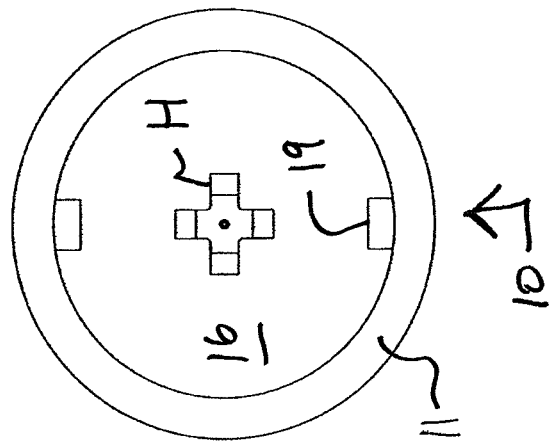
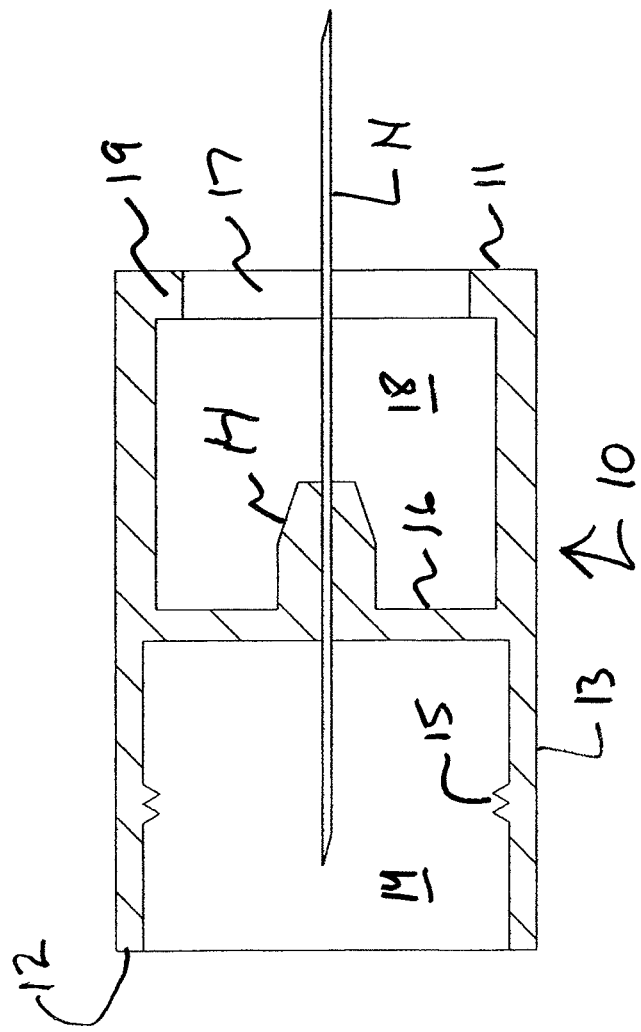

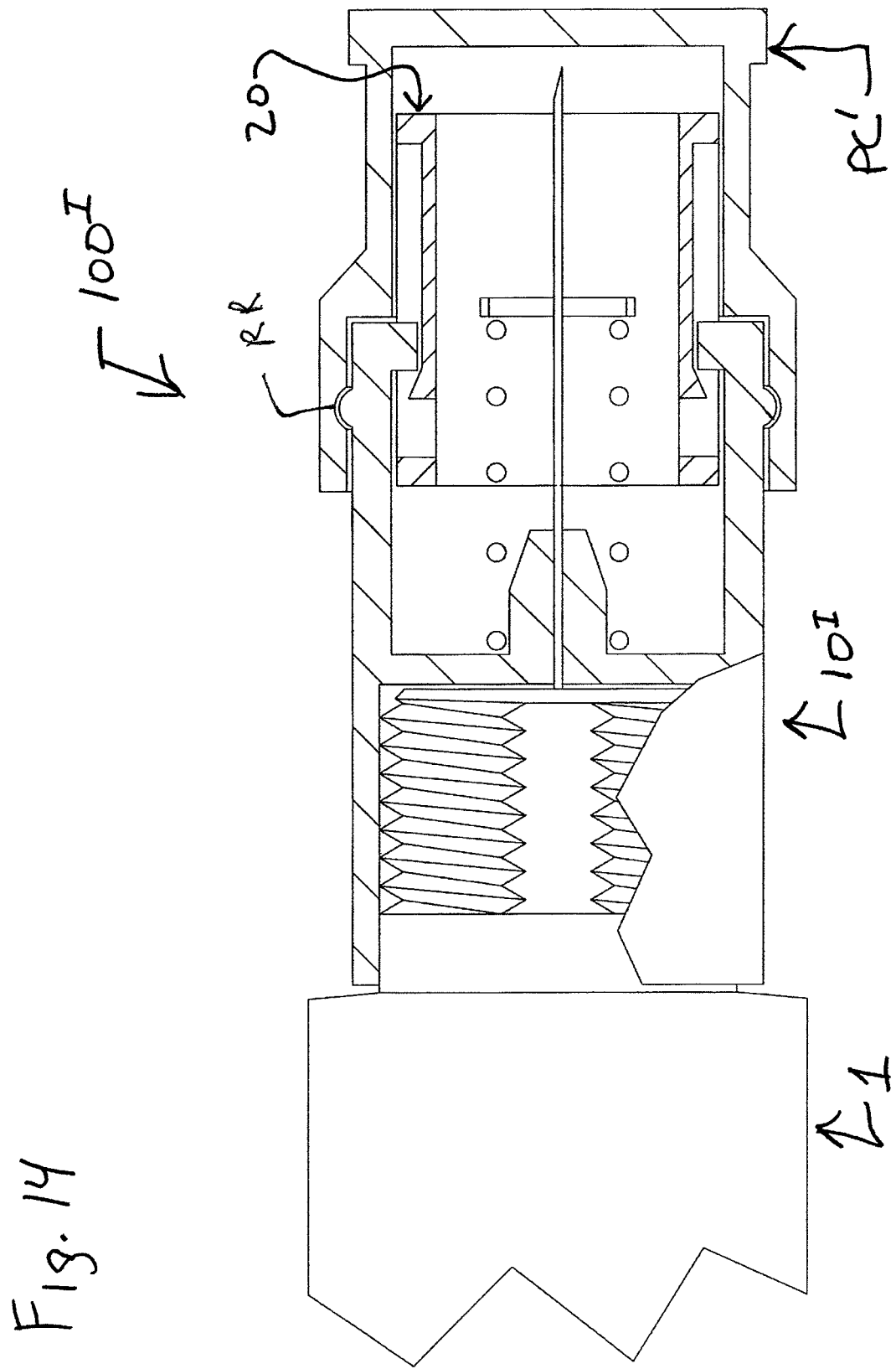

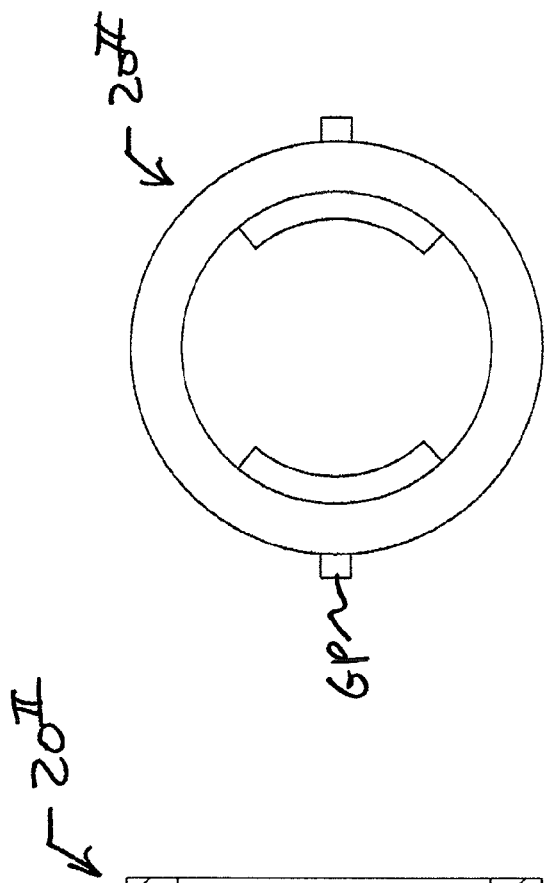
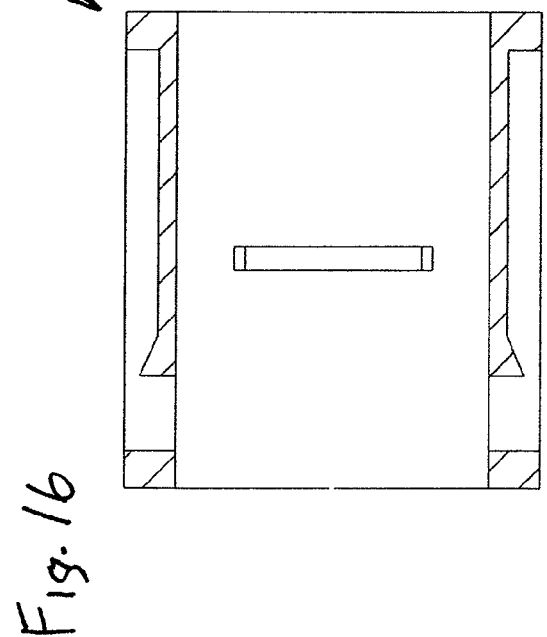
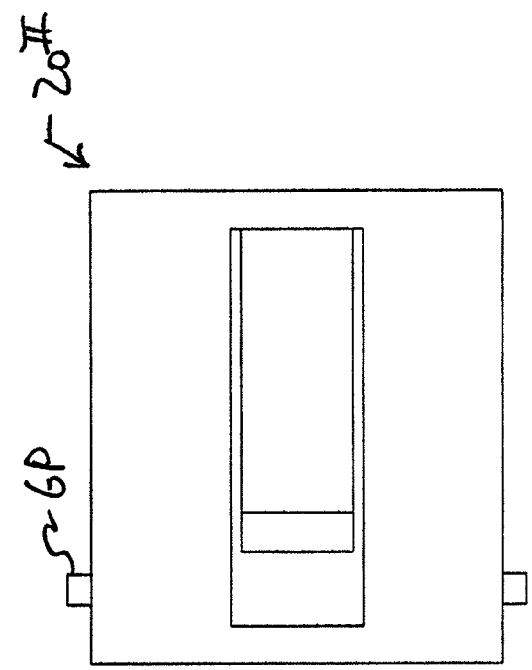
Fig. 16
Fig. 17
Fig. 18

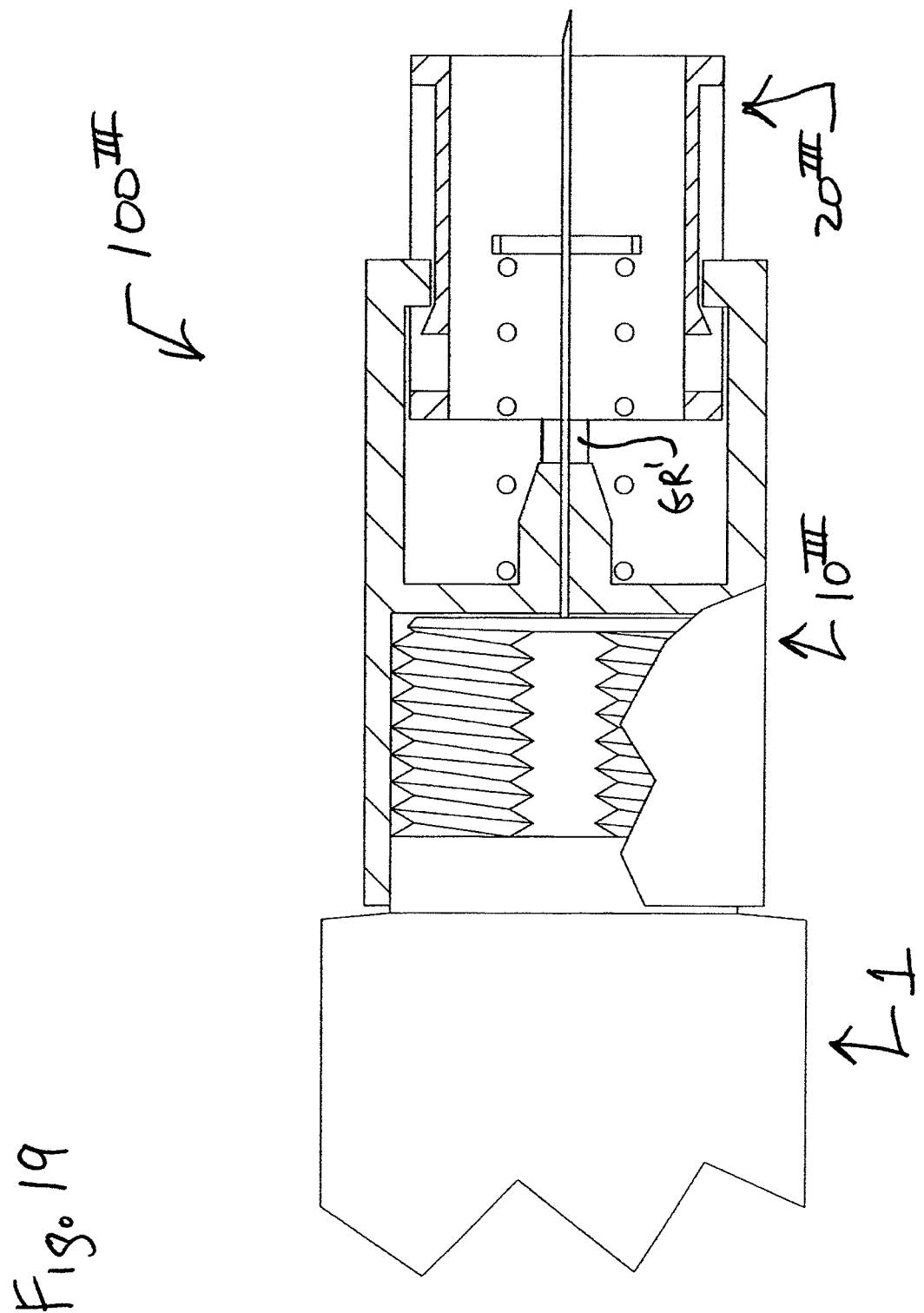

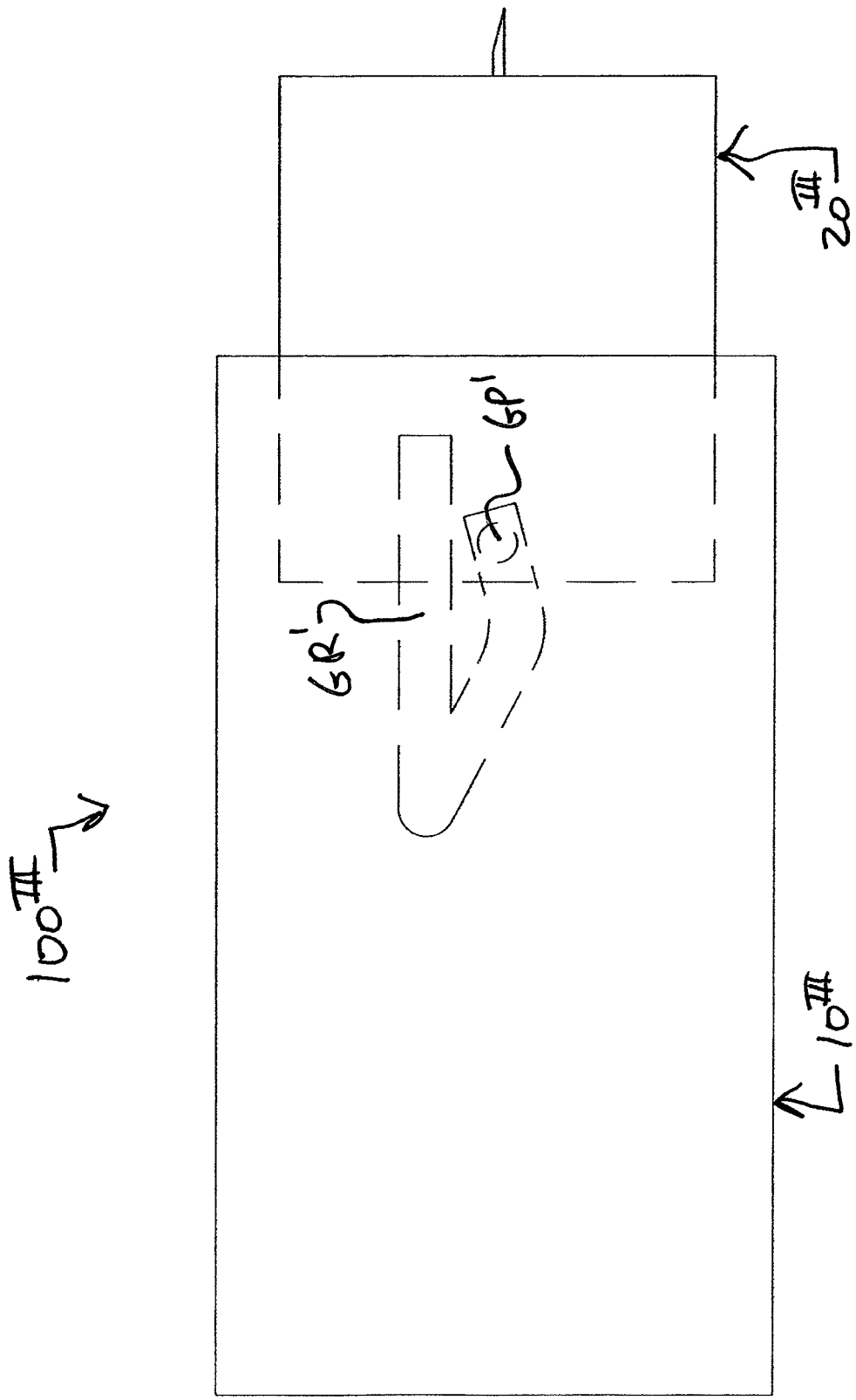

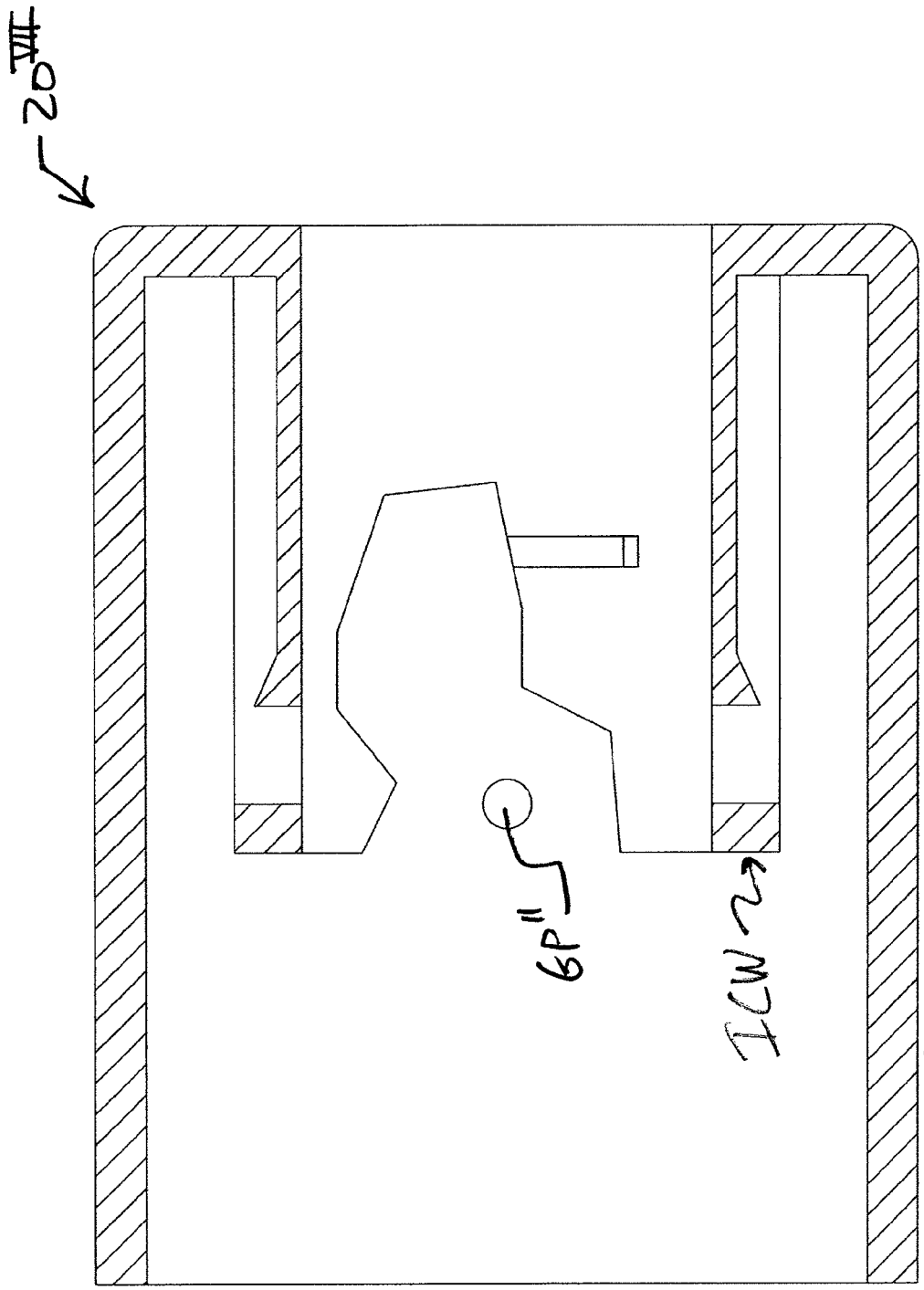

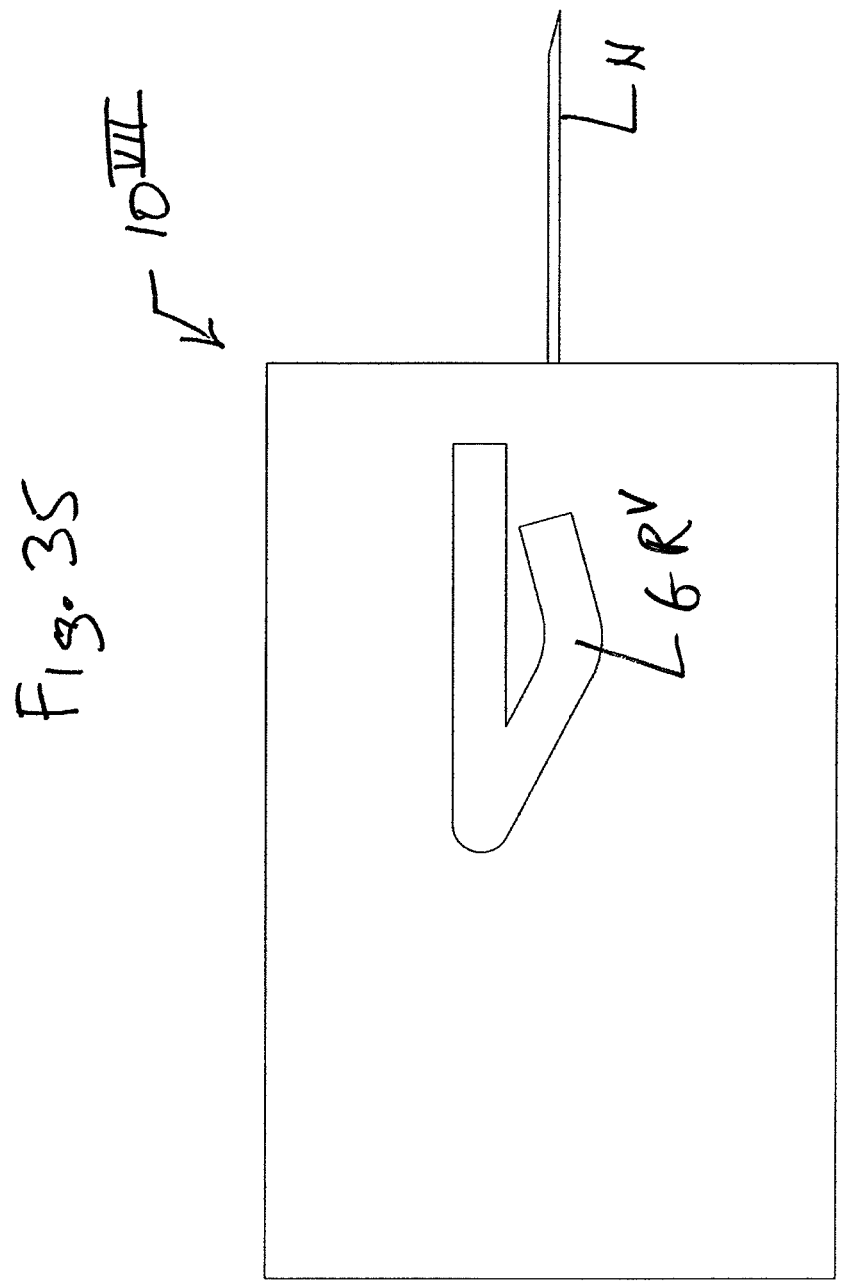

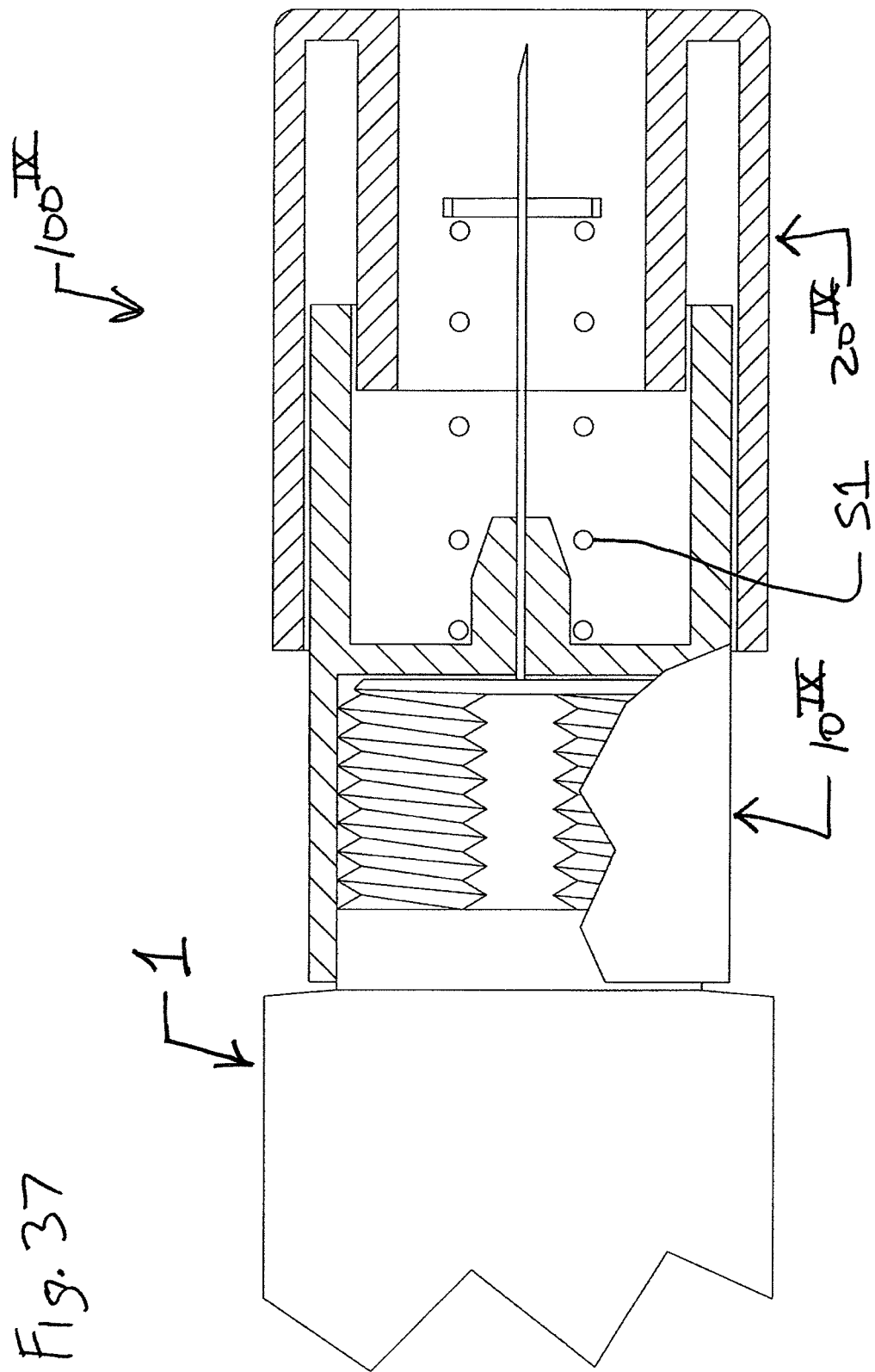

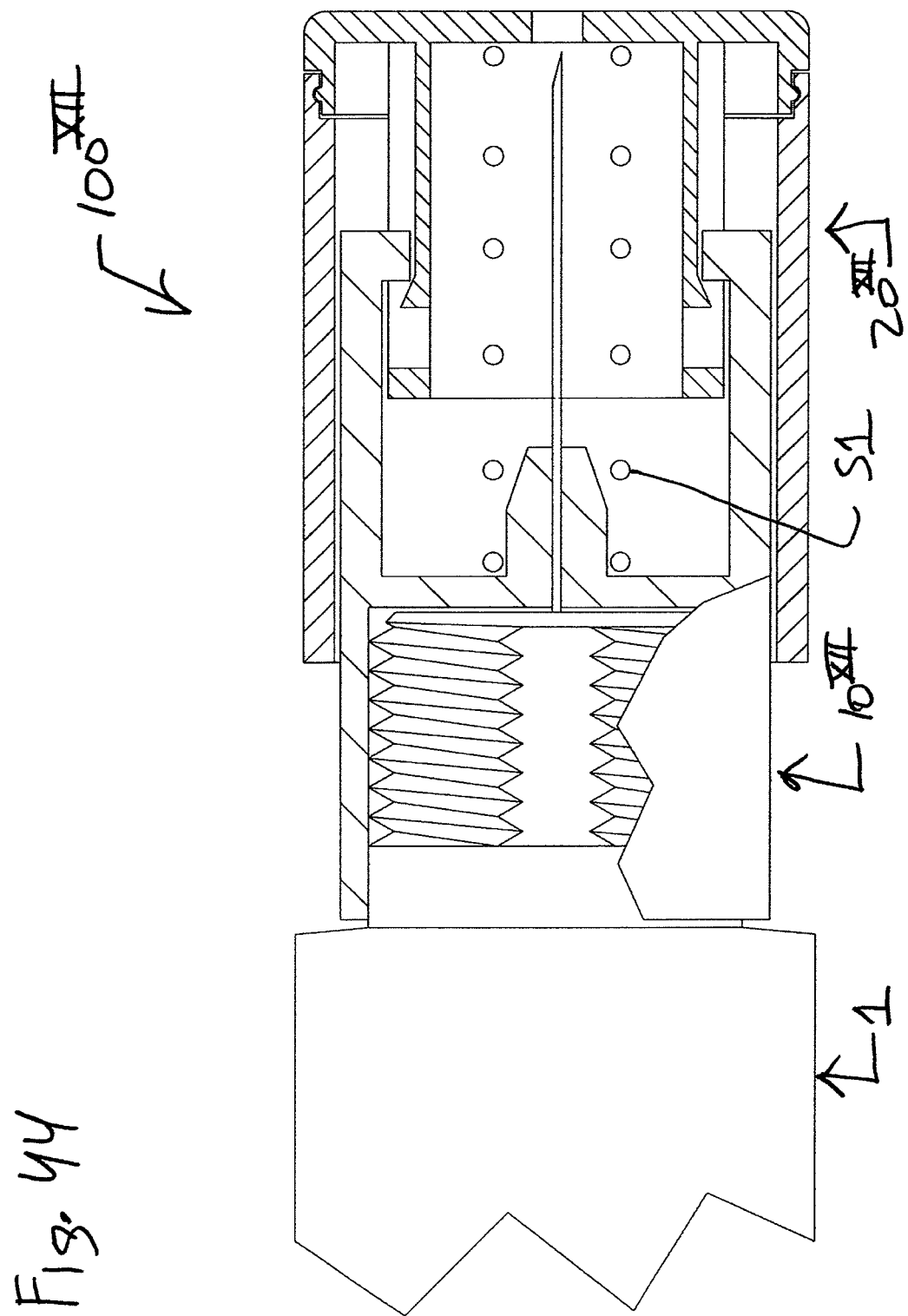

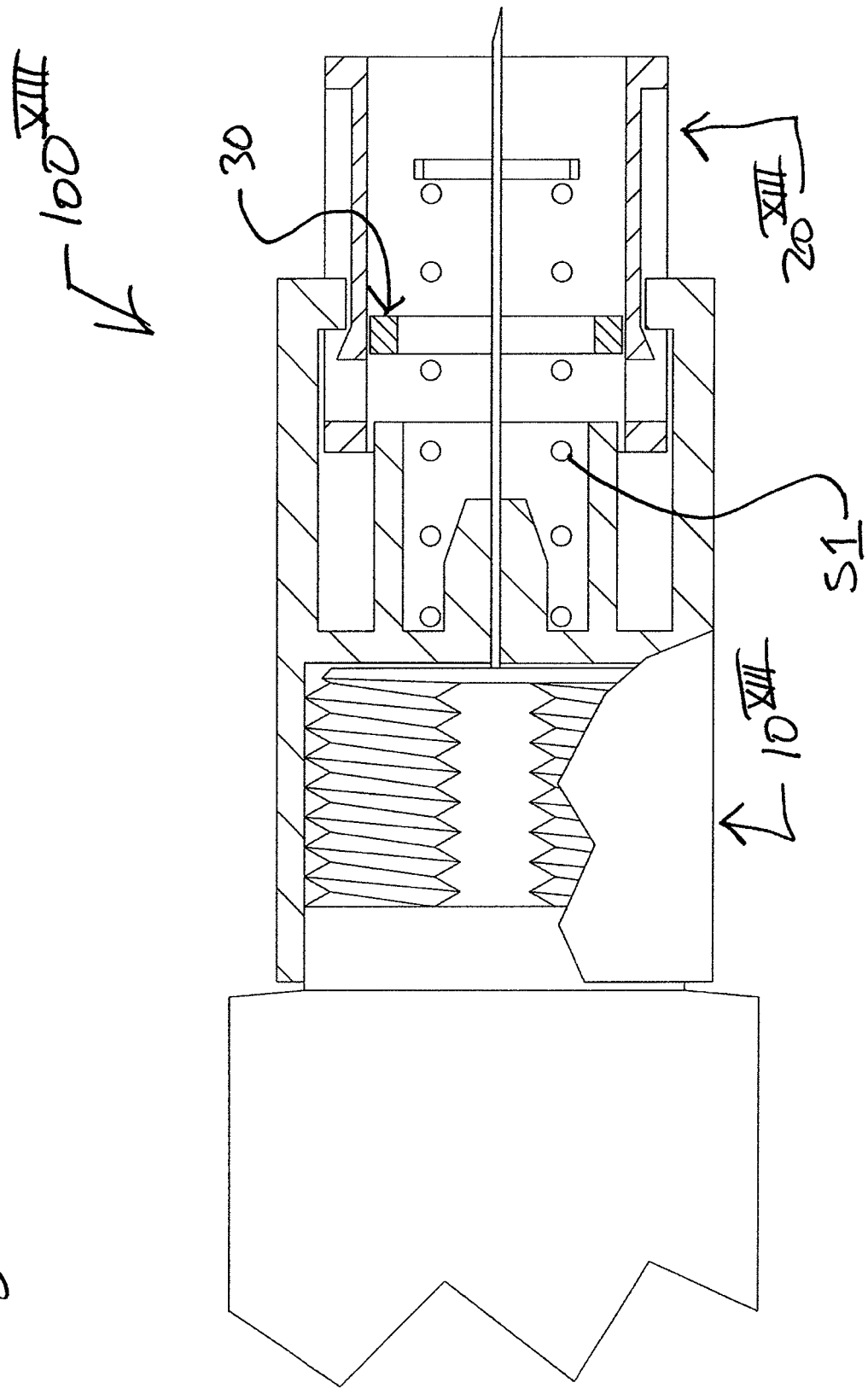

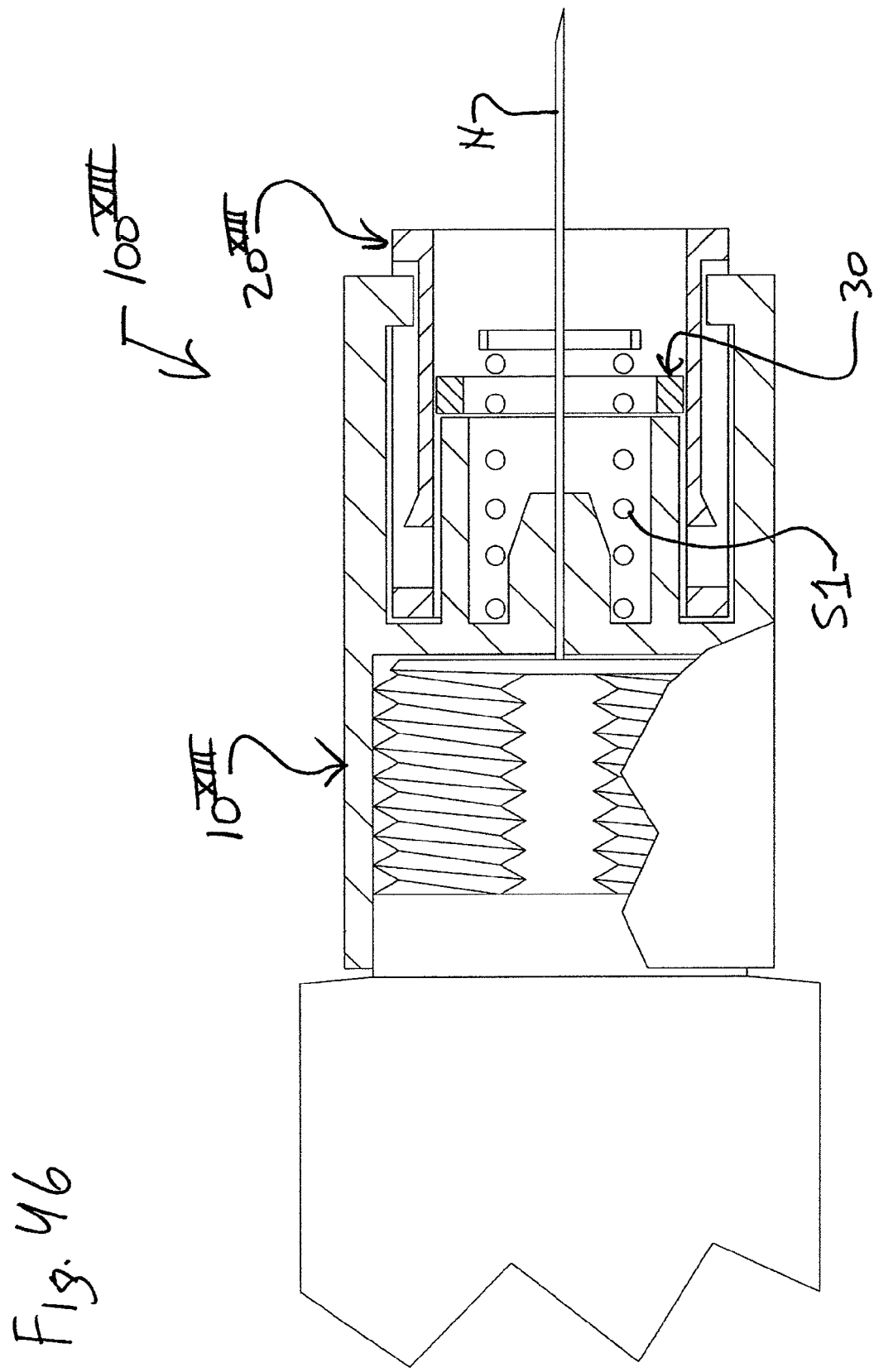

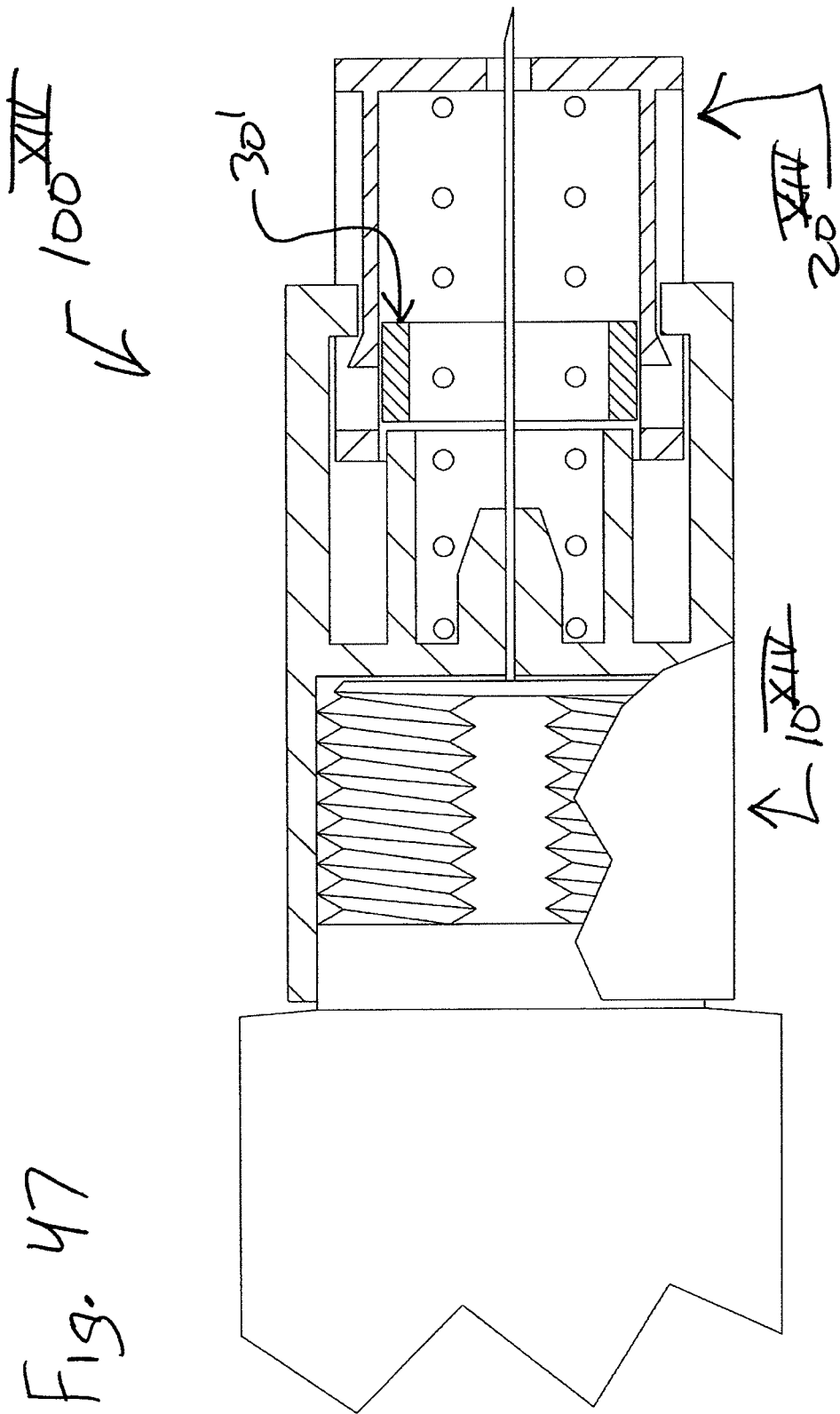

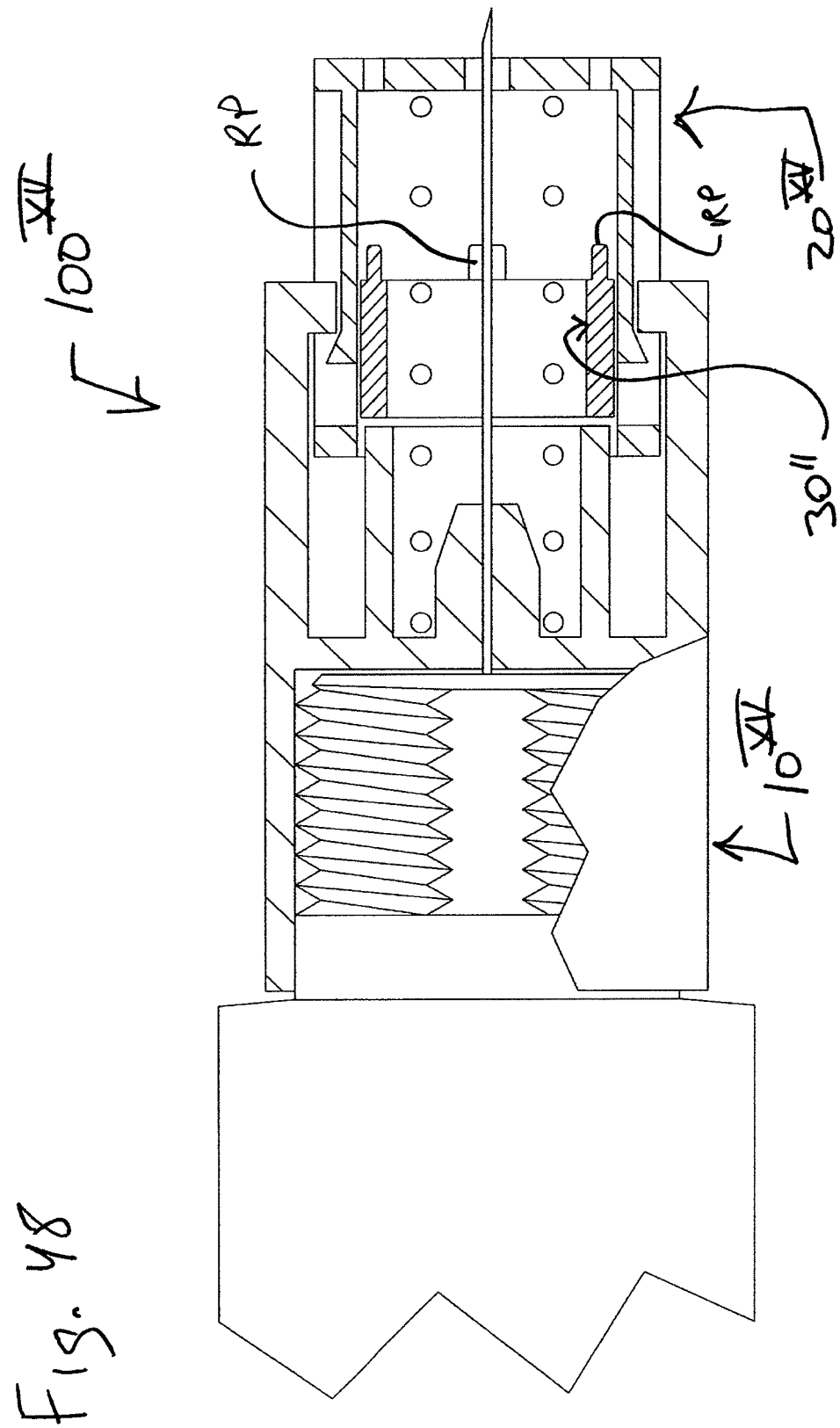

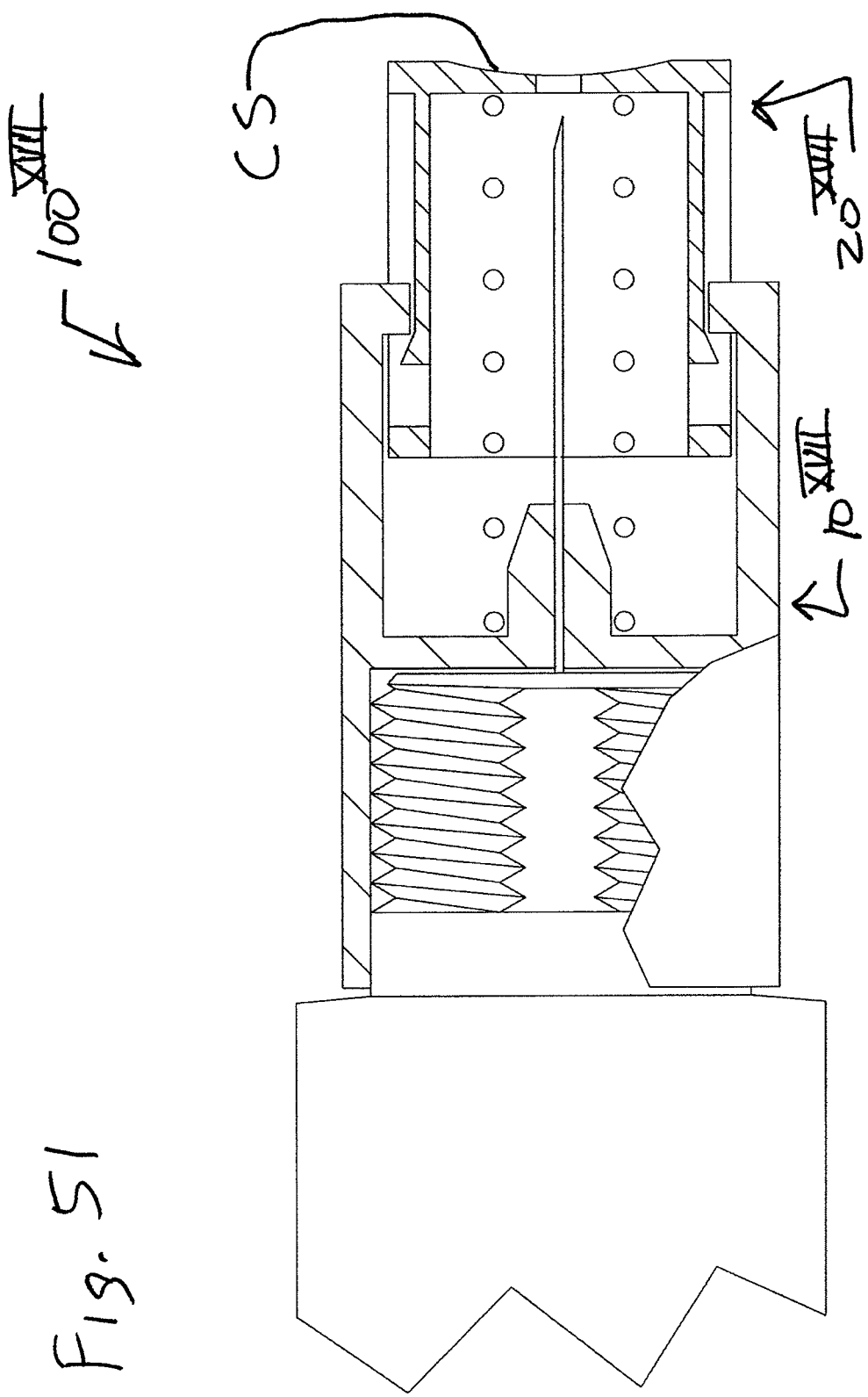

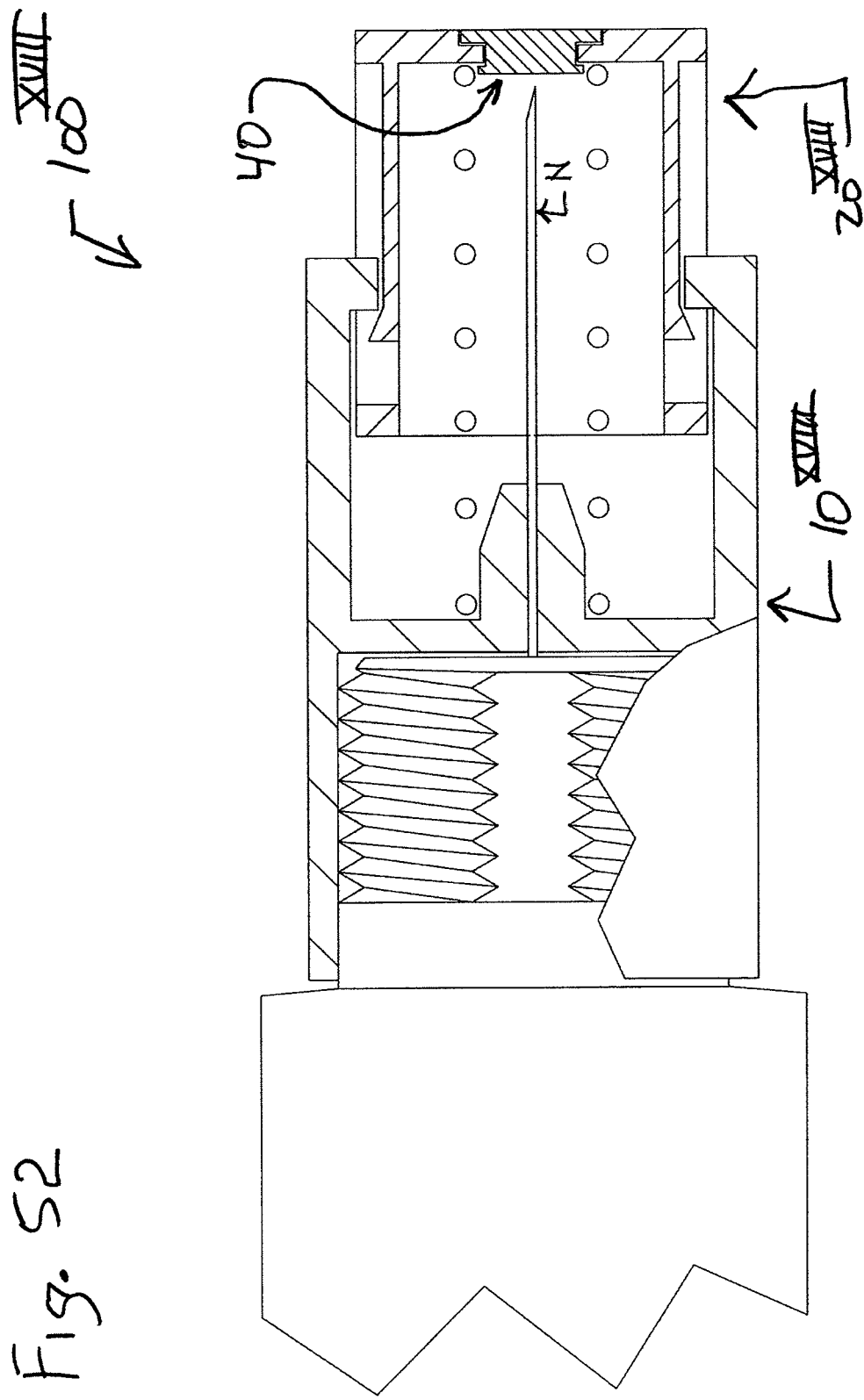

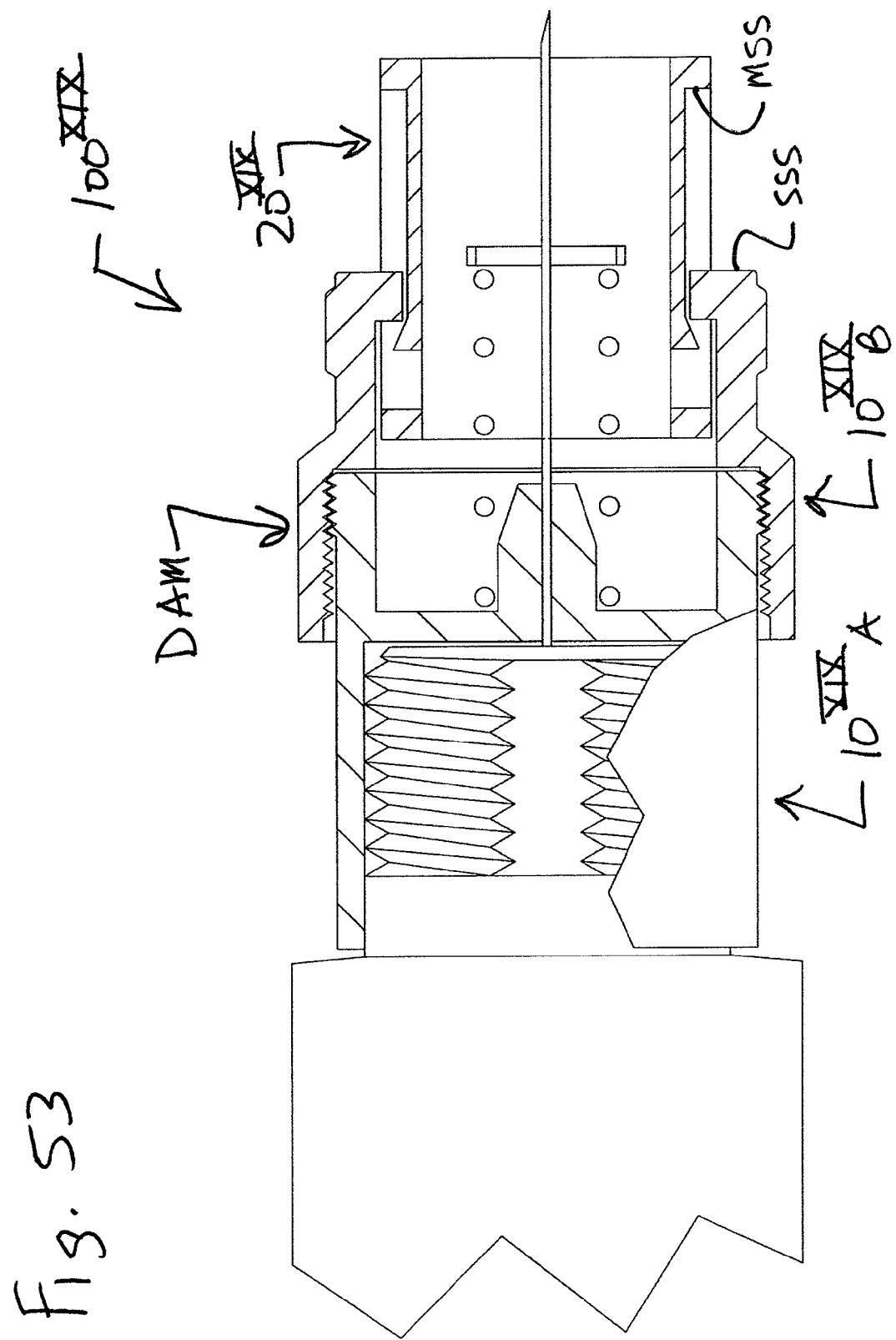

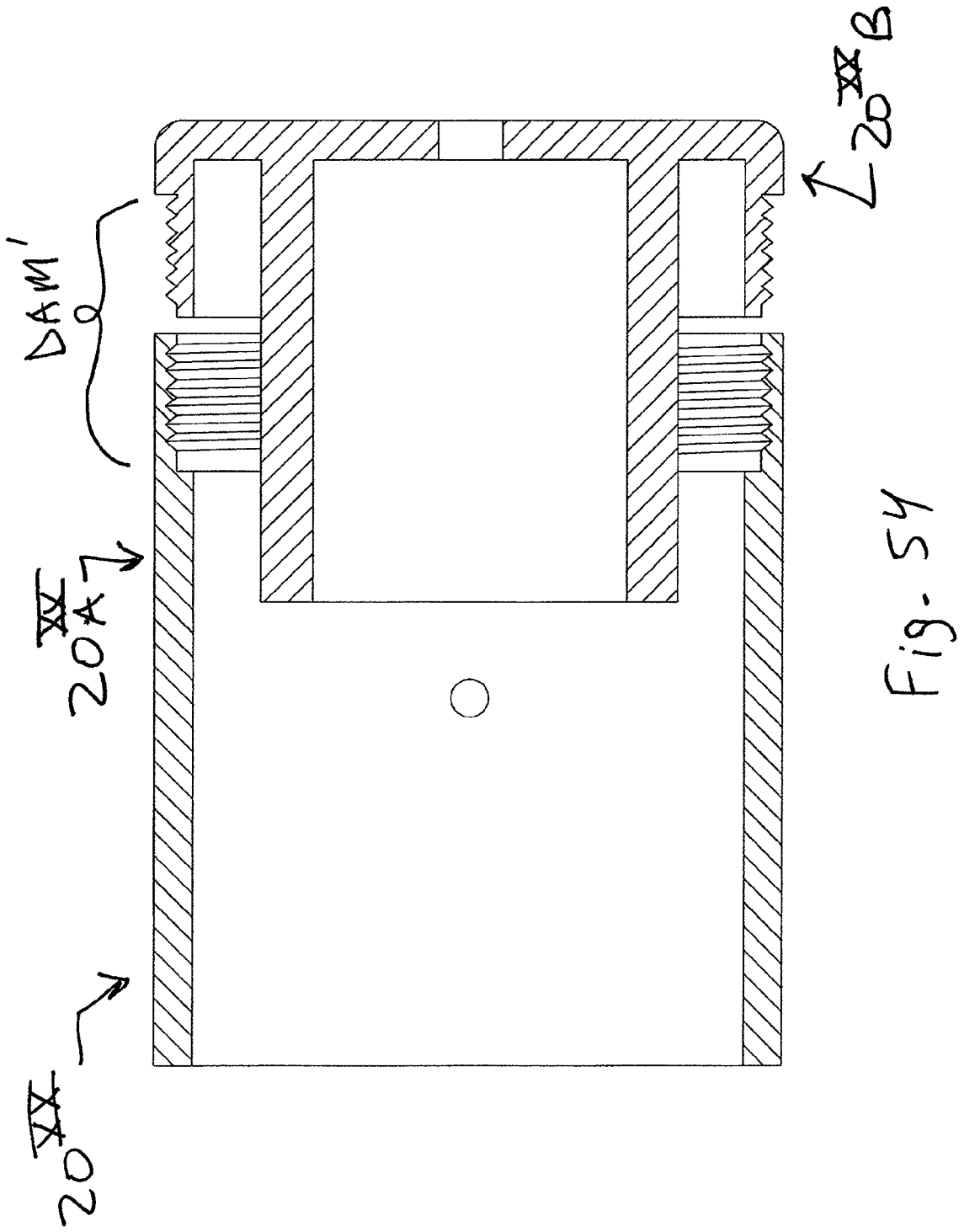

PEN NEEDLE WITH SAFETY SHIELD SYSTEM

CROSS-REFERENCE TO RELATED APPLICATIONS

The instant application is a U.S. non-provisional application that is based on and claims the benefit of U.S. provisional application No. 61/443,958, filed Feb. 17, 2011, the disclosure of which is hereby expressly incorporated by reference hereto in its entirety.

BACKGROUND OF THE INVENTION

1. Field of the Invention

This invention relates generally to pen injection devices, e.g., pre-loaded syringes, such as are utilized for injection of medicament into the body tissues of human and animal patients. More specifically, this invention relates to a removable pen needle which is more safely used and/or more safely easily installed and removed from a pen injection device. The pen needle can optionally include an arrangement that allows the pen needle to be installed axially without requiring it to be rotated and to also be removed axially without requiring it to be rotated.

This invention also relates to a method of using pen needles for pen injection devices wherein the pen needle is configured to be used with conventional pen injection devices.

This invention also relates to a method of using pen injection devices more safely, i.e., reducing the chance that the user will be pricked when handling and/or attempting to remove the pen needle from the pen injection device after use.

2. Discussion of Background Information

U.S. Pat. No. 4,973,318, the disclosure of which is hereby expressly incorporated by reference in its entirety, discloses a disposable syringe that includes first and second housing elements which are coupled together for rotation without axial movement therebetween. The first housing element receives a cartridge of a solution to be injected, and mounts a liquid outlet needle at its front end. A piston rod is disposed in the second housing element to move axially therein, and this piston rod includes a rod element and a nut element. The rod element is coupled to the first housing element to move axially therein without relative rotation therewith, and the nut element is threaded to the rod element for telescoping movement therewith and is configured to move axially in the second housing element without relative rotation therein. A pressure receiving element is mounted on the nut element. The housing, rod, nut and pressure receiving elements cooperate such that relative rotation between the housing elements in a selected direction causes relative rotation between the nut and rod elements and thereby increases the effective length of the piston rod and causes the pressure receiving element to extend from the second housing element. A protective cap is removably mounted over the first housing element and is configured to abut second housing element while mounted in place on the first housing element. This protective cap is engaged with the first housing element such that rotation of the cap with respect to the second housing element causes rotation of the first housing element with respect to the second housing element.

This type of syringe is shown in FIGS. 1 and 2 of U.S. Ser. No. 12/779,472 to SCHRAGA filed on May 13, 2010, the disclosure of which is hereby expressly incorporated by reference in its entirety, wherein the pre-loaded syringe 1 has a proximal threaded end 2 which is configured to accept a needle tip assembly consisting of a needle tip 5, a needle tip cover, and a needle cover. A user installs the needle tip assembly 5 onto the end 2, after removing the assembly from its individual package, onto the threaded proximal end 2 by simply sliding it onto the end 2 axially. Because internal threads of the needle tip 5 are mounted to radially deflectable members, installation over threads of the end 2 occurs with a ratchet effect. This installation is made safe by the covers which ensure that the user will not be pricked by the needle N. Once installed, the user can remove the needle tip cover by simply sliding it off axially. Next, the user can remove the needle cover to expose the needle N. The pen needle device is then made ready for use in providing an injection to the user. After injection, the user will typically remove the needle tip 5 and discard the same. To accomplish the removal, the user will typically reinstall the needle tip cover and rotate it to cause the needle tip to unthread from the threaded end 2 (some users may even install the needle cover prior to installing the cover). Once removed, however, it is still possible to reinstall the used needle tip 5 by simply repeating the steps noted above. Unless the user discards the needle tip 5, it is possible that she or other users will not remember or know that it has already been used. That is, there is nothing to prevent reuse of the needle tip 5 should someone attempt to reinstall the needle tip onto the end 2. Furthermore, if the user is unable to locate the covers (i.e., if they have become lost), he/she must then attempt to grip the needle tip 5 in order to unthread it from the end 2. As is apparent, this action can be risky because the user can possibly inadvertently be pricked by the needle N either in attempting to properly grip the needle tip 5, in the action of rotating it to the point it is removed, or even in the handling of the needle tip 5 after it has been removed and prior to being properly discarded. Still further, if the needle tip 5 is not properly discarded (such as being correctly placed in a sharps container), others may come in contact with the needle tip 5 and possibly become injured thereby.

The following documents, the disclosures of which are hereby expressly incorporated by reference in their entireties, discuss various ways in which needles can covered after use: US 2011/0022001 to WEI, U.S. Pat. No. 5,242,401 to COLSKY, U.S. Pat. No. 5,591,138 to VAILLANCOURT, U.S. Pat. No. 6,391,003 to LESCH, Jr., US 2002/0004648 to LARSEN et al., U.S. Pat. No. 7,540,858 to DIBIASI, U.S. Pat. No. 5,389,085 to D'ALESSIO et al., U.S. Pat. No. 4,894,055 to SUDNAK, U.S. Pat. No. 7,553,293 to JENSEN et al., U.S. Pat. No. 6,855,129 to JENSEN et al., and US 2005/0038392 to DESALVO. Such documents, however, are either not related to pen needles or disclose safety systems for pen needles which lack one or more features of the invention, and the advantages thereof.

It is therefore desirable to provide a pen needle system which is safer to use and/or easier to make compared to the conventional devices discussed above.

SUMMARY OF THE INVENTION

According to one non-limiting embodiment of the invention, there is provided a needle tip for an injection device comprising a body having a front portion, a back portion configured to be removably connected to the pre-loaded injection device, and a wall separating the front and back portions, a hollow needle having a first piercing portion projecting back from the separating wall and a second piercing portion projecting forward from the separating wall, and a safety shield that is axially movable relative to the body at least between an initial position, a retracted position, and a post use locking position.

In embodiments, the safety shield at least is at least partially disposed within the front portion of the body, includes a locking system which is prevented from being contacted by a user's fingers, and moves linearly without also rotating.

In embodiments, the safety shield at least rotates at least partially in one direction as it moves from the initial position to the retracted position.

In embodiments, the safety shield at least rotates at least partially in opposite directions as it moves from the initial position to the retracted position;

In embodiments, the safety shield at least includes at least one projection that extends into a guide recess comprising at least a linear section and a curved section.

In embodiments, the safety shield at least includes at least one projection that extends into a guide recess comprising at least a linear section and an angled section.

In embodiments, the safety shield at least includes at least one projection that extends into a guide recess comprising at least one locking mechanism for retaining the safety shield in the post use locking position.

In embodiments, the safety shield at least includes at least one mechanism for preventing a locking of the safety shield when said shield in not in the post use locking position.

In embodiments, the safety shield at least includes at least one mechanism for providing a visual indication to the user that the needle tip has been used, wherein the visual indication is arranged on a skin engaging end of the safety shield.

In embodiments, the safety shield at least includes at least one mechanism for providing a tactile indication to the user that the needle tip has been used.

In embodiments, the safety shield at least includes a first portion that is at least partially disposed within the front portion of the body, a second portion that at least partially covers the front portion, has its movement limited by engagement between at least one projection extending into a guide recess.

In embodiments, the body comprises at least one projection for engaging an external thread of a proximal end of the injection device.

In embodiments, once installed, the needle tip threadably engages with a proximal end of the injection device.

In embodiments, the body comprises at least one partial internal thread section for engaging an external thread of a proximal end of the injection device.

In embodiments, the tip further comprises a spring for biasing the safety shield away from the retracted position.

In embodiments, the safety shield, when in the initial position, does not cover or extend out past a free end of the second piercing portion.

In embodiments, the safety shield, when in the initial position, does cover or extend out past a free end of the second piercing portion.

In embodiments, the safety shield includes at least one depth adjustment mechanism for controlling a depth of injection.

In embodiments, the safety shield is movably mounted to the body and the body includes at least one depth adjustment mechanism for controlling a depth of injection.

In embodiments, the safety shield includes at least one pierceable member that is pierced during injection.

In embodiments, the safety shield includes at least one pierceable and resealable member that is pierced during injection.

In embodiments, there is provided a method of removing the tip described above, wherein the method comprises installing the tip onto a proximal end of an injection device, using the tip to inject a substance, and after the safety shield automatically moves to the post use locking position, removing the tip.

According to one non-limiting embodiment of the invention, there is provided a pre-filled injection device comprising a pre-filled injection device body and a removable pen needle installed on the pre-filled injection device body, wherein the pen needle comprises a body having a front portion, a back portion configured to be removably connected to the pre-loaded injection device, and a wall separating the front and back portions; a hollow needle having a first piercing portion projecting back from the separating wall and a second piercing portion projecting forward from the separating wall; a safety shield that is axially movable relative to the body at least between an initial position, a retracted position, and a post use locking position, wherein the safety shield at least one of: is at least partially disposed within the front portion of the body, includes a locking system which is prevented from being contacted by a user's fingers, and moves linearly without also rotating; rotates at least partially in opposite directions as it moves from the initial position to the retracted position; rotates at least partially in opposite directions as it moves from the initial position to the retracted position; includes at least one projection that extends into a guide recess comprising at least a linear section and a curved section; includes at least one projection that extends into a guide recess comprising at least a linear section and an angled section; includes at least one projection that extends into a guide recess comprising at least one locking mechanism for retaining the safety shield in the post use locking position; includes at least one mechanism for preventing a locking of the safety shield when said shield in not in the post use locking position; includes at least one mechanism for providing a visual indication to the user that the needle tip has been used, wherein the visual indication is arranged on a skin engaging end of the safety shield; includes at least one depth adjustment mechanism for controlling a depth of injection; is movably mounted to the body and the body includes at least one depth adjustment mechanism for controlling a depth of injection; includes at least one pierceable member that is pierced during injection; includes at least one pierceable and resealable member that is pierced during injection; includes at least one mechanism for providing a tactile indication to the user that the needle tip has been used; and the safety shield and includes a first portion that is at least partially disposed within the front portion of the body, a second portion that at least partially covers the front portion, has its movement limited by engagement between at least one projection extending into a guide recess.

According to one non-limiting embodiment of the invention, there is provided a pen needle comprising a body having a front portion, a back portion configured to be removably connected to the pre-loaded injection device, and a wall separating the front and back portions, a hollow needle having a first piercing portion projecting back from the separating wall and a second piercing portion projecting forward from the separating wall, and a safety shield that is axially movable relative to the body at least between an initial position, a retracted position, and a post use locking position, wherein the safety shield at least one of: is at least partially disposed within the front portion of the body, includes a locking system which is prevented from being contacted by a user's fingers, and moves linearly without also rotating; rotates at least partially in opposite directions as it moves from the initial position to the retracted position; rotates at least partially in opposite directions as it moves from the initial position to the retracted position; includes at least one projection that extends into a guide recess comprising at least a linear section and a curved section; includes at least one projection that extends into a guide recess comprising at least a linear section and an angled section; includes at least one projection that extends into a guide recess comprising at least one locking mechanism for retaining the safety shield in the post use locking position; includes at least one mechanism for preventing a locking of the safety shield when said shield in not in the post use locking position; includes at least one mechanism for providing a visual indication to the user that the needle tip has been used, wherein the visual indication is arranged on a skin engaging end of the safety shield; includes at least one mechanism for providing a tactile indication to the user that the needle tip has been used; includes at least one depth adjustment mechanism for controlling a depth of injection; is movably mounted to the body and the body includes at least one depth adjustment mechanism for controlling a depth of injection; includes at least one pierceable member that is pierced during injection; includes at least one pierceable and resealable member that is pierced during injection; and includes a first portion that is at least partially disposed within the front portion of the body, a second portion that at least partially covers the front portion, has its movement limited by engagement between at least one projection extending into a guide recess.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 1-13 show a first non-limiting embodiment of the pen needle or needle tip in accordance with the invention. In FIGS. 1-9 and 11, for example, the body, shield, spring and protective cover are shown in full or partial cross-section while the injector, threaded section and needle are not;

FIG. 14 shows a second non-limiting embodiment of the pen needle or needle tip in accordance with the invention;

FIGS. 15-18 show a third non-limiting embodiment of the pen needle or needle tip in accordance with the invention;

FIGS. 19-22 show a fourth non-limiting embodiment of the pen needle or needle tip in accordance with the invention;

FIGS. 23-26 illustrates how the fourth non-limiting embodiment of the pen needle or needle tip is used in accordance with the invention;

FIGS. 31-35 show an eight non-limiting embodiment of the pen needle or needle tip in accordance with the invention;

FIG. 36 shows a ninth non-limiting embodiment of the pen needle or needle tip in accordance with the invention;

FIGS. 37-39 show a tenth non-limiting embodiment of the pen needle or needle tip in accordance with the invention;

FIG. 44 shows a thirteenth non-limiting embodiment of the pen needle or needle tip in accordance with the invention;

FIGS. 45-46 show a fourteenth non-limiting embodiment of the pen needle or needle tip in accordance with the invention;

FIG. 47 shows a fifteenth non-limiting embodiment of the pen needle or needle tip in accordance with the invention;

FIGS. 48-49 show a sixteenth non-limiting embodiment of the pen needle or needle tip in accordance with the invention;

FIG. 51 shows a eighteenth non-limiting embodiment of the pen needle or needle tip in accordance with the invention;

FIG. 52 shows a nineteenth non-limiting embodiment of the pen needle or needle tip in accordance with the invention;

FIG. 53 shows a twentieth non-limiting embodiment of the pen needle or needle tip in accordance with the invention; and FIG. 54 shows a twenty first non-limiting embodiment of the pen needle or needle tip in accordance with the invention.

DETAILED DESCRIPTION OF THE INVENTION

Figure 1:
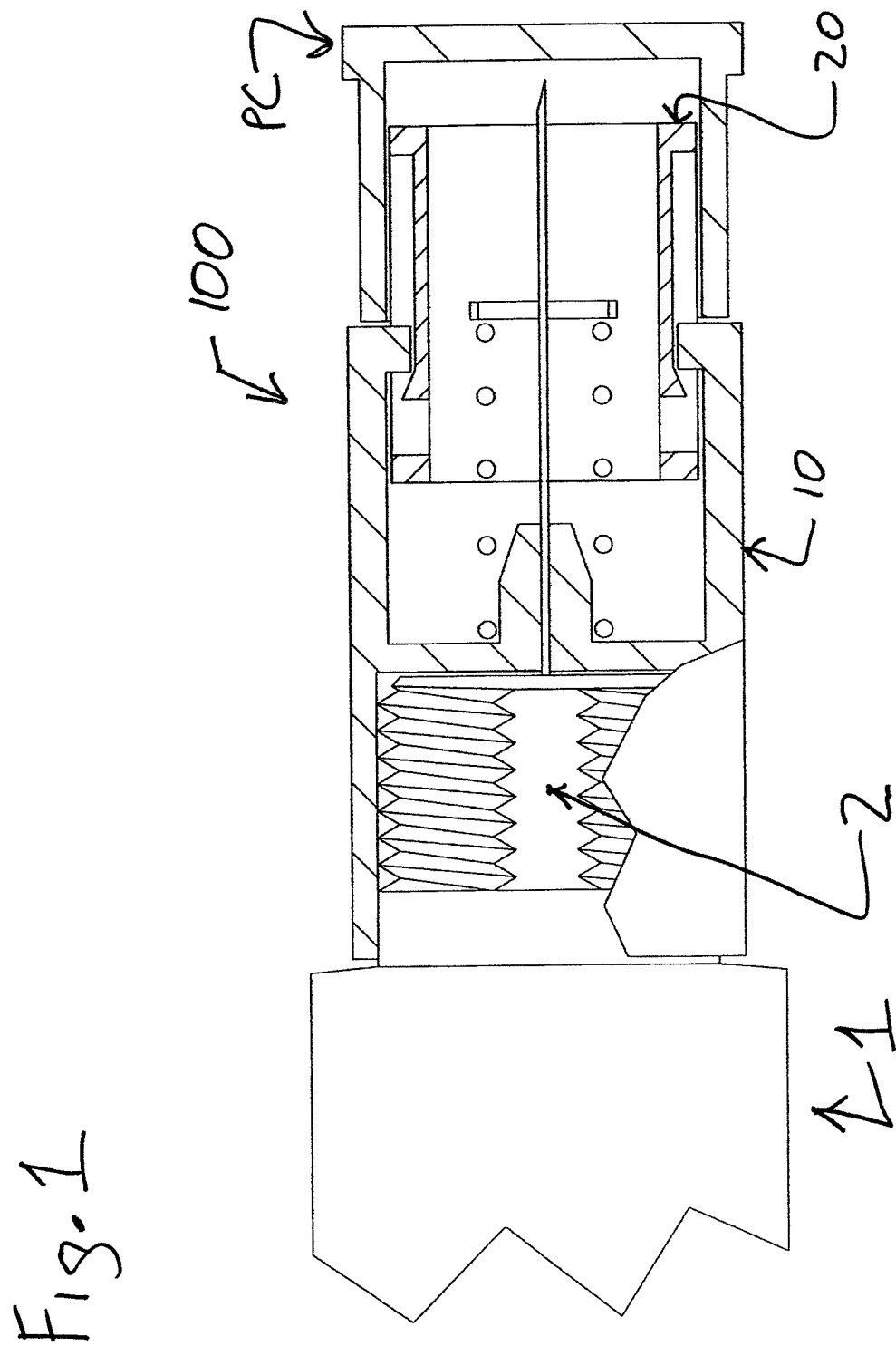

FIGS. 1-13 show a first non-limiting embodiment of the pen needle or needle tip 100 in accordance with the invention. The needle tip 100 has a rear or distal portion that is removably connected, e.g., threadably connected, to the threaded section 2 of a pen needle injection device 1. More specifically, the needle tip 100 has a body portion 10, e.g., one-piece or integrally formed body, and a safety shield 20, e.g., a one-piece or integrally formed safety shield. In embodiments, a protective cap or cover PC is utilized so that the needle tip 100 can be safely packaged, shipped and/or installed on the injector 1. Once the needle tip 100 is installed, the protective cap PC can be removed and even discarded.

Figure 2:
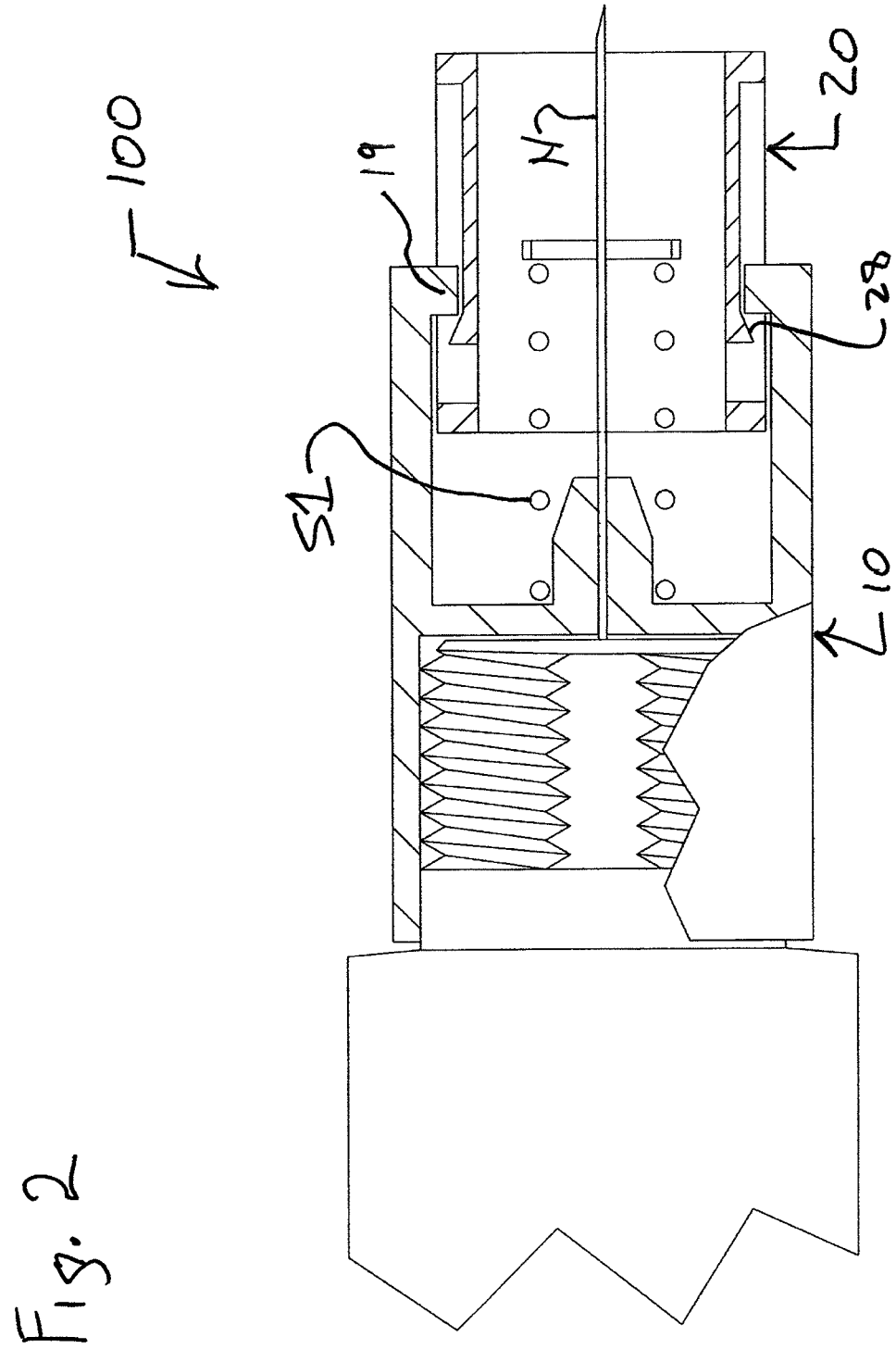

In the position shown in FIG. 2, the safety-shield 20 of the needle tip 100 is in an intermediate position. In this position, (and after the protective cap PC is removed) the safety-shield 20 is free to move generally axially. For example, the safety-shield 20 shown in FIG. 2 does not extend out all the way so as to cover the proximal needle N. This allows a user to see the needle tip so that he/she can accurately position the needle N at a desired injection location. The position of the shield 20 shown in FIG. 2 is essentially determined by the biasing force of the spring S1 and contact between projections 28 and shoulders or projections 19 of the body 10.

Figure 3:
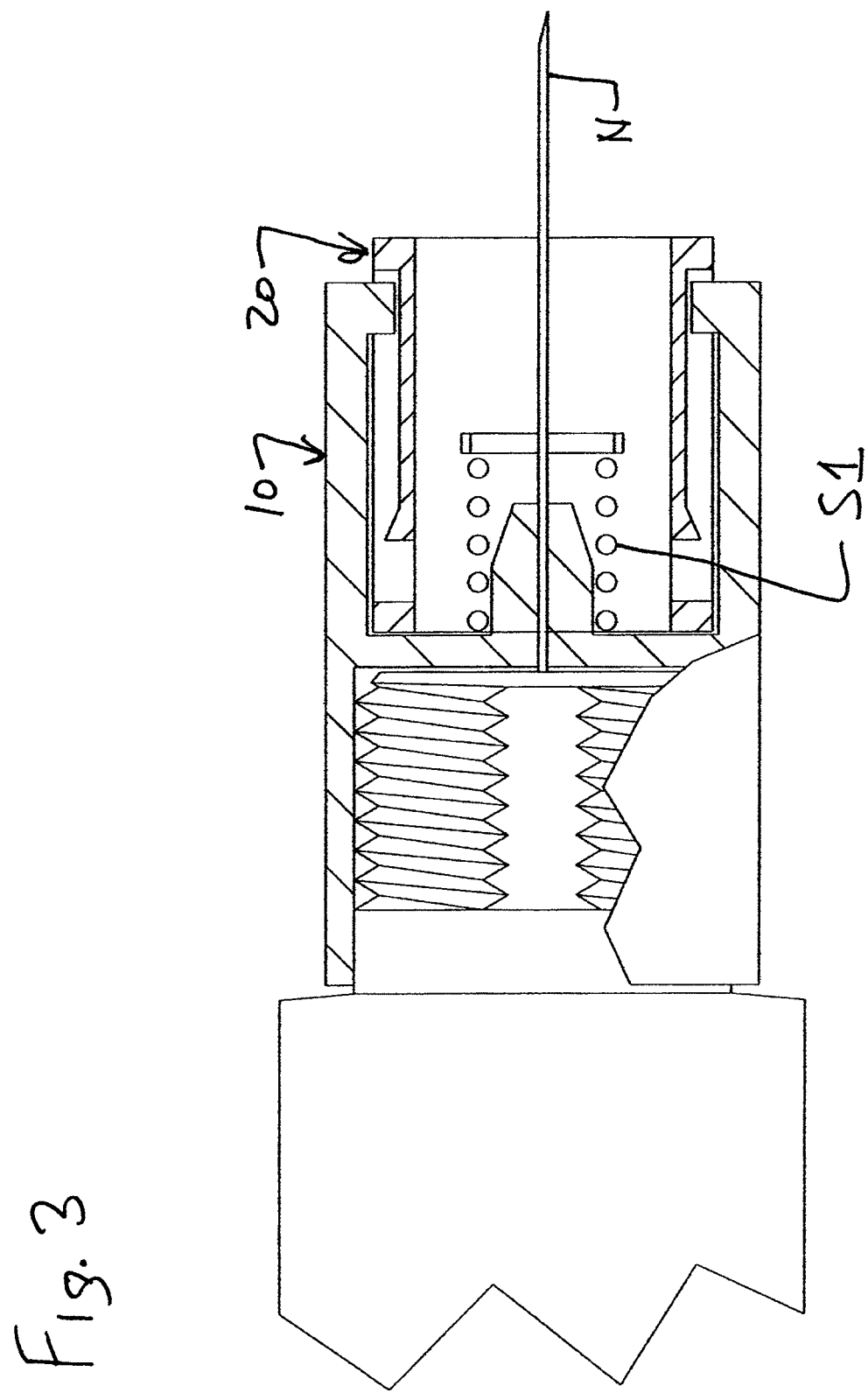

In the position shown in FIG. 3, the safety-shield 20 of the needle tip 100 is in a puncturing or retracted position. In this position, the safety-shield 20 is typically pressed against a skin surface being injected with a force sufficient to cause compression of the spring S1 and to move the shield 20 to the fully or nearly fully retracted position from the initial or intermediate position shown in FIG. 2. For example, the safety-shield 20 shown in FIG. 3 exposes a maximum amount of the needle N available for injection. The maximum axial retraction movement of the shield 20 can be made or set to a desired amount by, e.g. setting the relative location or position of contact between surface 22 and wall 16 (see FIG. 4). The maximum axial retraction movement can also occur alternatively or simultaneously via setting the relative location or position of contact between each surface 29 and projection 19.

Figure 4:
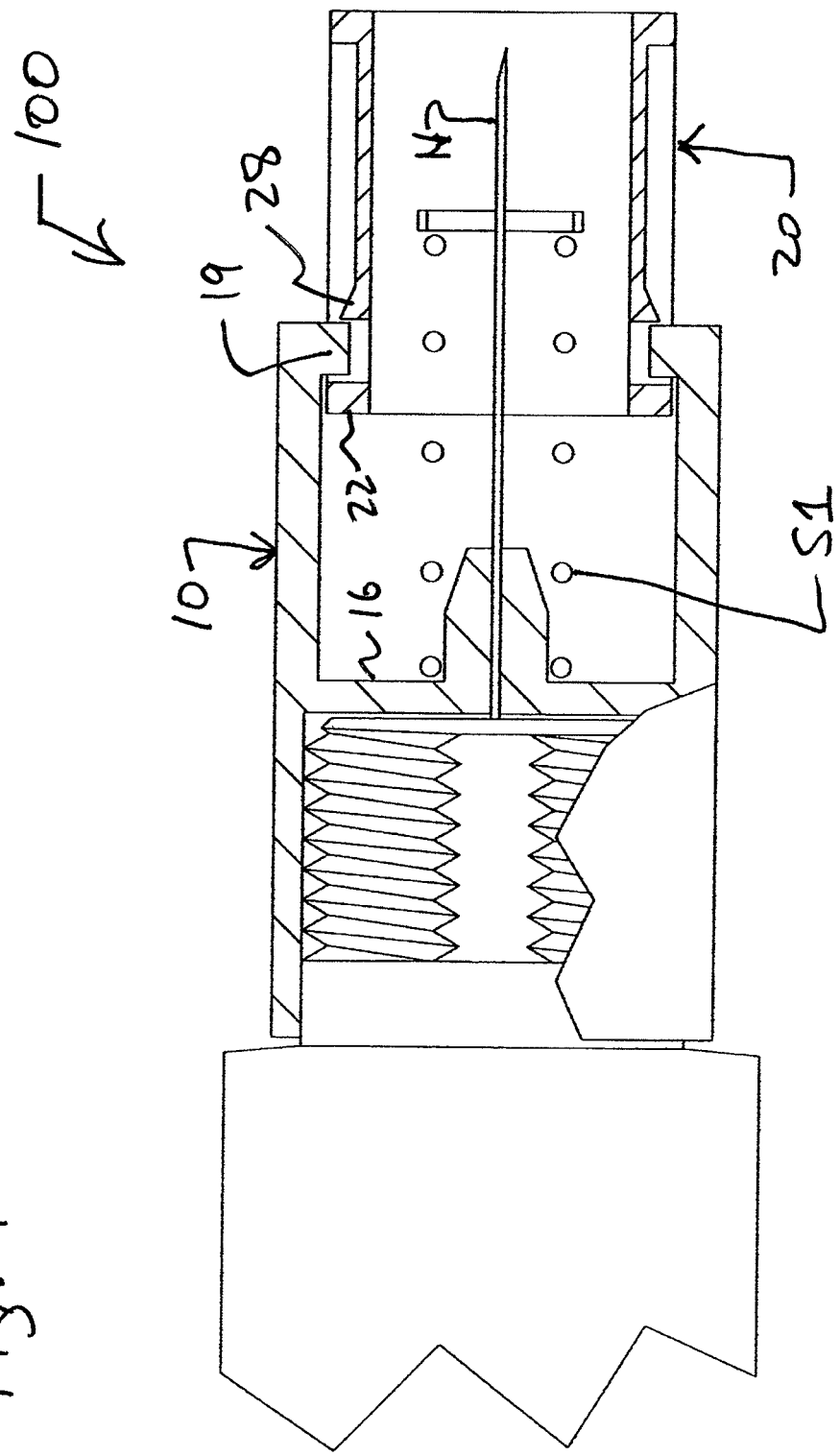

In the position shown in FIG. 4, the safety-shield 20 of the needle tip 100 is in a locked, non-removably and fully or nearly fully extended position. In this position, the safety-shield 20 has automatically moved from that shown in FIG. 3 to that of FIG. 4 under the action or biasing force of the spring S1 and which has occurred very rapidly. That is, once the user stops pressing the needle tip 100 against the injection site, the spring S1 responds or axially expands essentially instantaneously and causes forward movement of the shield 20 toward the position shown in FIG. 4. However, this rapid axial expansion of the spring S1 coupled with the mass of the shield 20 provides sufficient energy or momentum so that the shield 20 is able to move past or beyond the position shown in FIG. 2 and to, in fact, reach the locked position shown in FIG. 4. Much of this energy is used to cause deflection of the deflectable members 27 so that the tapered projections 28 can pass by the projections 19. Once past by the projections 19, the projections 28 spring back to an original position shown in FIG. 4. Moreover, because of the tapered shape or configuration of the projections 28, the shield 20 cannot move back more than a very slight amount and cannot move by an amount which would expose the tip of the needle N. Thus, the recesses 25 serve to trap the projections 19 and prevent significant axial movement of shield 20 either forwards or backwards. Additionally, because the projections 28 are recessed within grooves containing therein the deflectable members 27, a user cannot easily cause the projections 28 to deflect inwardly so as to intentionally release the locked configuration shown in FIG. 4. Even if this was done, however, the force of the spring S1 would have to be overcome (by causing the shield 20 to move backwards) to allow the needle N to be exposed to the user. Nor can the user easily (without causing damage to the tip 100) remove the shield 20 from the body 10 by pulling it off, for example. Even a tilting or sideways deflection of the shield 20 relative to the body 10 is prevented or limited by the interaction between the projections 19 and the recesses or openings 25. Further still, because of the locked configuration shown in FIG. 4, the needle tip 100 is prevented from re-use and is thereby rendered a single-use tip 100. The user thus has no option by to remove the tip 100 from the injection device 1 and to discard it.

As is apparent from FIG. 5, removal of the tip 100 can be safely accomplished because the needle N is covered by the shield 20. Such removal can occur in the typical manner by, e.g., unthreading it off of the threaded section 2. Once removed, one can see from FIG. 5 that both the rear or distal needle and the front needle are covered, protected or otherwise not exposed.

Figure 8:
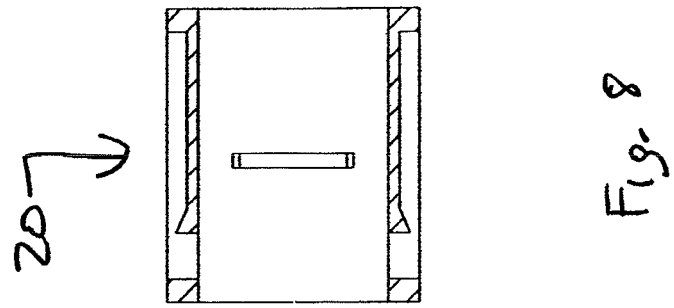
Figure 7:
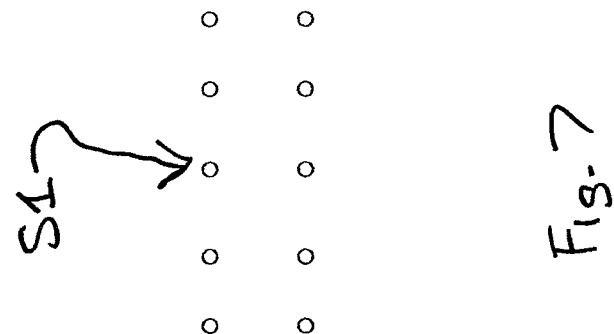
Figure 6:
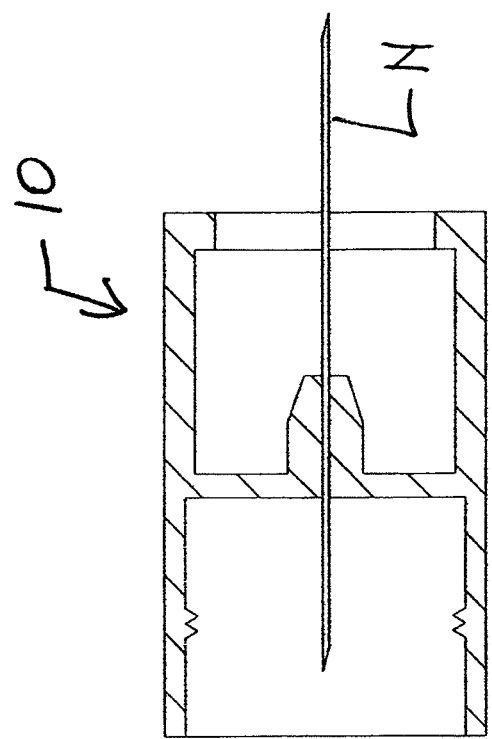

As is apparent from FIGS. 6-8, the needle tip 100 has three main components, i.e., a body 10 containing therein a hollow double-ended needle N, a wire compression spring S1, and a shield 20. Both the body 10 and the shield 20 can preferably be made of synthetic resin with the exception of the needle N which can be made of metal such a stainless steel. The spring S1 can also be made of metal such a stainless steel.

As is apparent from FIGS. 9 and 10, the body 10 includes a forward or proximal end 11, a rear or distal end 12, a generally cylindrical outer surface 13, a rear or distal inner space 14 sized and configured to receive therein the threaded section 2, one or more threads, thread sections, or partial thread sections 15 configured to threadably engage with the threads of the threaded section 2, a separating wall 16 containing a hub H that fixedly retains the double-ended needle N, a front opening 17 that received therein the shield 20, a front or proximal inner space 18 sized and configured to receive therein the shield 20, and plural equally spaced or oppositely arranged inward facing or oriented projections 19.

Figure 13:
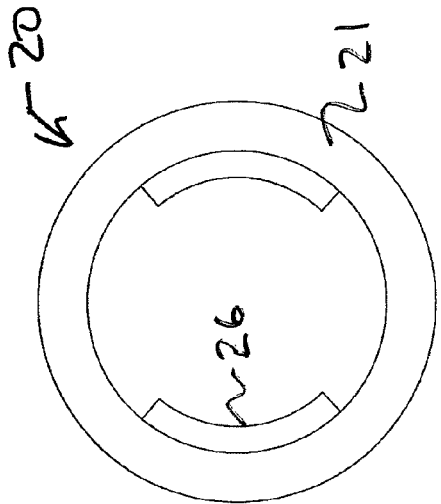
Figure 11:
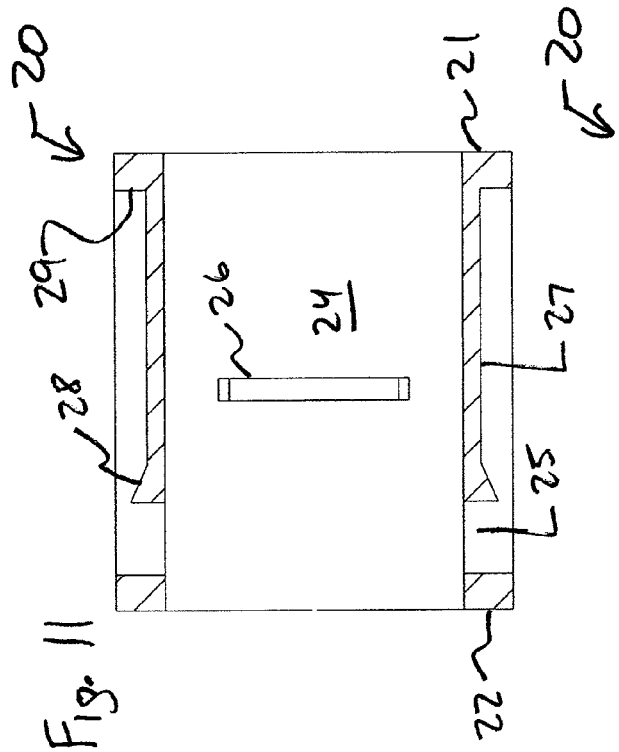
Figure 12:
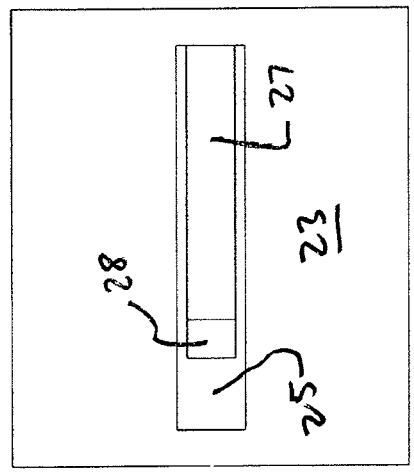
Figure 15:
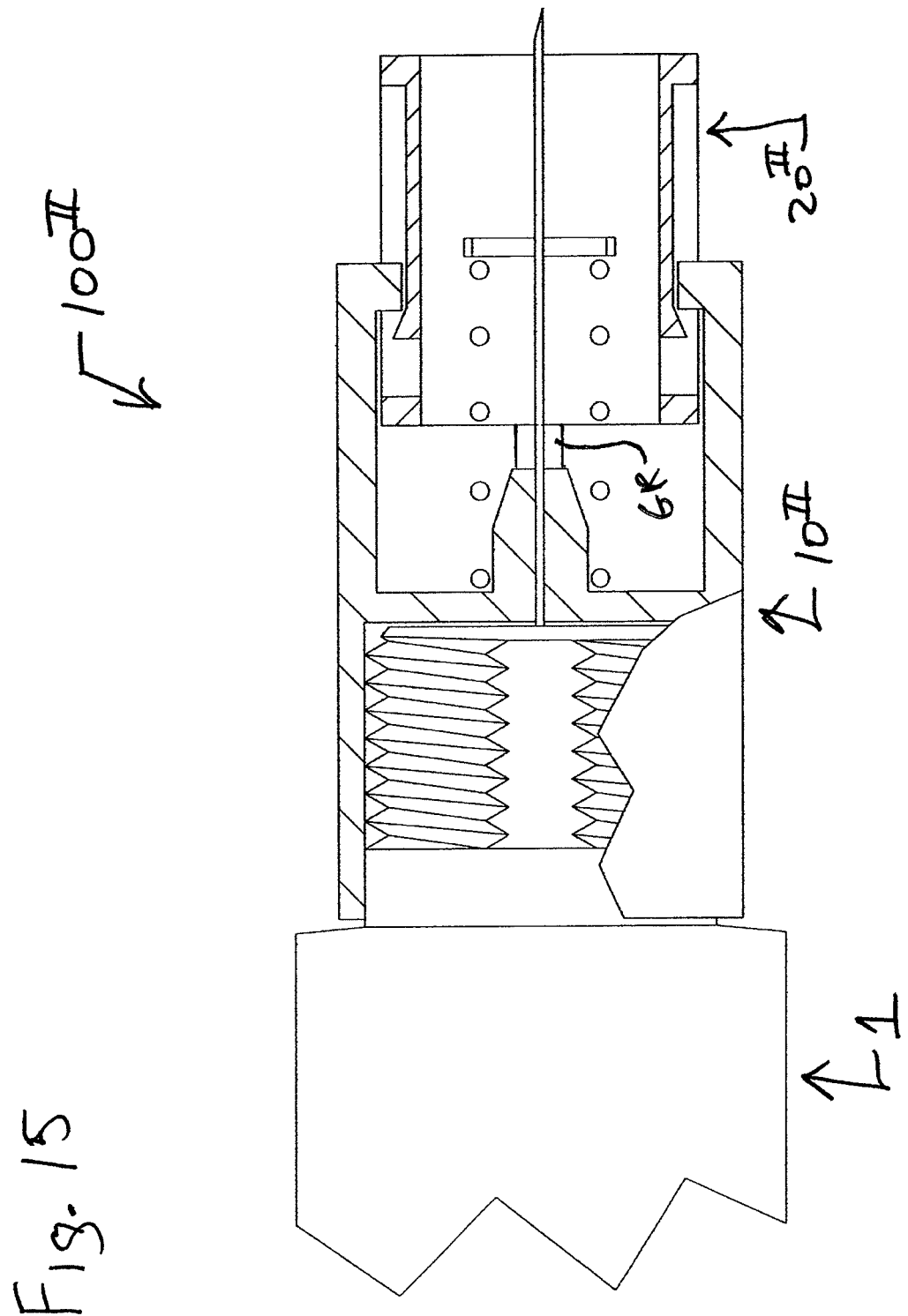
Figure 22:
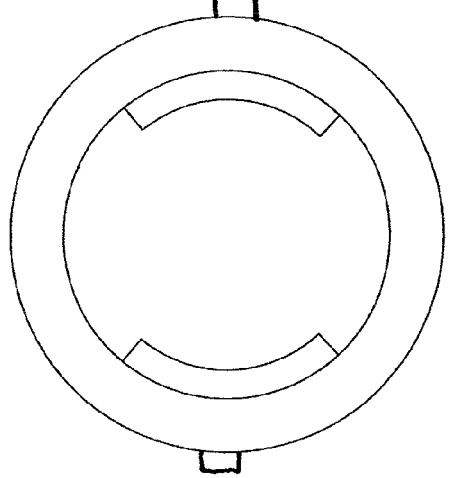
Figure 20:
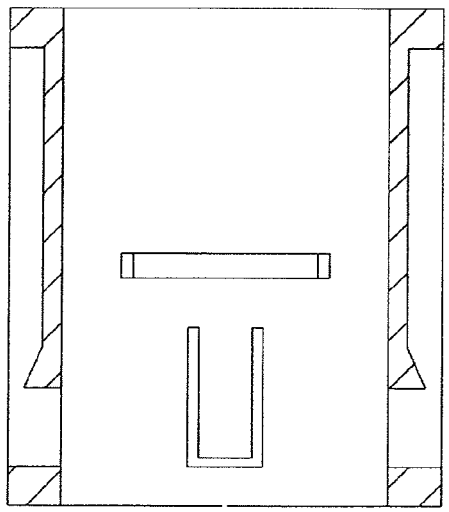
Figure 21:
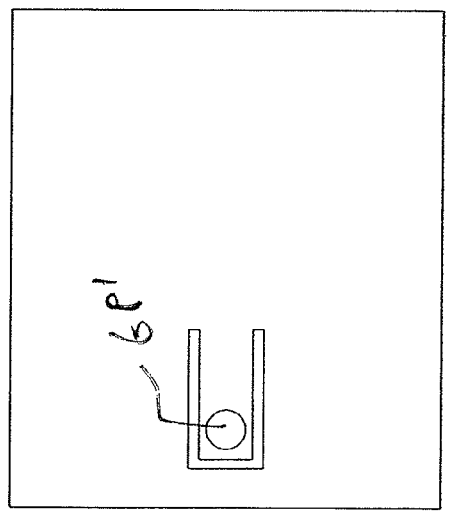

As is apparent from FIGS. 11-13, the shield 20 includes a forward or proximal end 21, a rear or distal end 22, a generally cylindrical outer surface 23, a main inner space 24, plural oppositely arranged recesses 25, plural oppositely arranged retaining flanges or shoulders 26 contacted by one end of the spring S1, plural oppositely arranged deflecting or deflectable members 27 each having a tapered projection 28. Oppositely arranged inner shoulders 29 are arranged on the shield 20.

Thus, in the non-limiting embodiment of FIGS. 1-13, there is provided a needle tip 100 for an injection device 1 which includes a body 10 having a front portion, a back portion configured to be removably connected to the pre-loaded injection device 1, and a wall 16 or needle support H separating the front and back portions. A hollow needle N has a first piercing portion projecting back from the separating wall 16 or needle support H and a second piercing portion projecting forward from the separating wall 16 or needle support H. A safety shield 20 is axially movable relative to the body 10 at least between an initial position (see FIG. 2), a retracted position (see FIG. 3), and a post use locking position (see FIG. 4).

Also, in the non-limiting embodiment of FIGS. 1-13, the safety shield 20, in embodiments, is at least partially disposed within the front portion of the body 10, e.g., end 22 is arranged within space 18, includes a locking system, e.g., one or more elements 28/25/19, which is prevented from being contacted by a user's fingers, and moves linearly, e.g., axially linearly, without also rotating, e.g., the interaction of the projections 19 with the guiding grooves containing the deflectable members 27 prevents rotation of the shield 20 relative to the body 10.

Also or alternatively, in the non-limiting embodiment of FIGS. 1-13, the safety shield 20, in embodiments, includes at least one projection 19 that extends into a guide recess comprising at least one locking mechanism 25/28 for retaining the safety shield 20 in the post use locking position (see FIG. 4).

Also or alternatively, in the non-limiting embodiment of FIGS. 1-13, the safety shield 20, in embodiments, includes at least one mechanism 28 for preventing a locking of the safety shield 20 when said shield in not in the post use locking position, i.e., is in the intermediate position shown in FIG. 2.

FIG. 14 shows another non-limiting embodiment of the pen needle or needle tip $100^I$ in accordance with the invention. The needle tip $100^I$ has a rear or distal portion that is removably connected, e.g., threadably connected, to the threaded section 2 of a pen needle injection device 1. More specifically, the needle tip $100^I$ has a body portion $10^I$, e.g., one-piece or integrally formed body, and a safety shield 20, e.g., a one-piece or integrally formed safety shield. In embodiments, a protective cap or cover PC' is utilized so that the needle tip $100^I$ can be safely packaged, shipped and/or installed on the injector 1. Once the needle tip $100^I$ is installed, the protective cap PC' can be removed and even discarded. Although similar to that of FIGS. 1-13, the protective cap PC' includes one or more retaining recesses RR which engage with one or more retaining projections RP arranged on the body $10^I$.

FIGS. 15-18 show another non-limiting embodiment of the pen needle or needle tip $100^{II}$ in accordance with the invention. The needle tip $100^{II}$ has a rear or distal portion that is removably connected, e.g., threadably connected, to the threaded section 2 of a pen needle injection device 1. More specifically, the needle tip $100^{II}$ has a body portion $10^{II}$, e.g., one-piece or integrally formed body, and a safety shield $20^{II}$, e.g., a one-piece or integrally formed safety shield. In embodiments, a protective cap or cover can be utilized (not shown) so that the needle tip $100^{II}$ can be safely packaged, shipped and/or installed on the injector 1. Once the needle tip $100^{II}$ is installed, the protective cap can be removed and even discarded. Although similar to that of FIGS. 1-13, the needle shield $20^{II}$ includes oppositely arranged guiding projections GP which engage with one or more guiding recesses GR arranged on the body $10^{II}$.

FIGS. 19-26 show another non-limiting embodiment of the pen needle or needle tip $100^{III}$ in accordance with the invention. The needle tip $100^{II}$ has a rear or distal portion that is removably connected, e.g., threadably connected, to the threaded section 2 of a pen needle injection device 1. More specifically, the needle tip $100^{III}$ has a body portion $10^{III}$, e.g., one-piece or integrally formed body, and a safety shield $20^{III}$, e.g., a one-piece or integrally formed safety shield. In embodiments, a protective cap or cover can be utilized (not shown) so that the needle tip $100^{III}$ can be safely packaged, shipped and/or installed on the injector 1. Once the needle tip $100^{III}$ is installed, the protective cap can be removed and even discarded. Although similar to that of FIGS. 15-18, the needle shield $20^{III}$ includes oppositely arranged guiding projections GP' which can deflect inwardly and engage with one or more guiding recesses GR' arranged on the body $10^{III}$.

Figure 24:
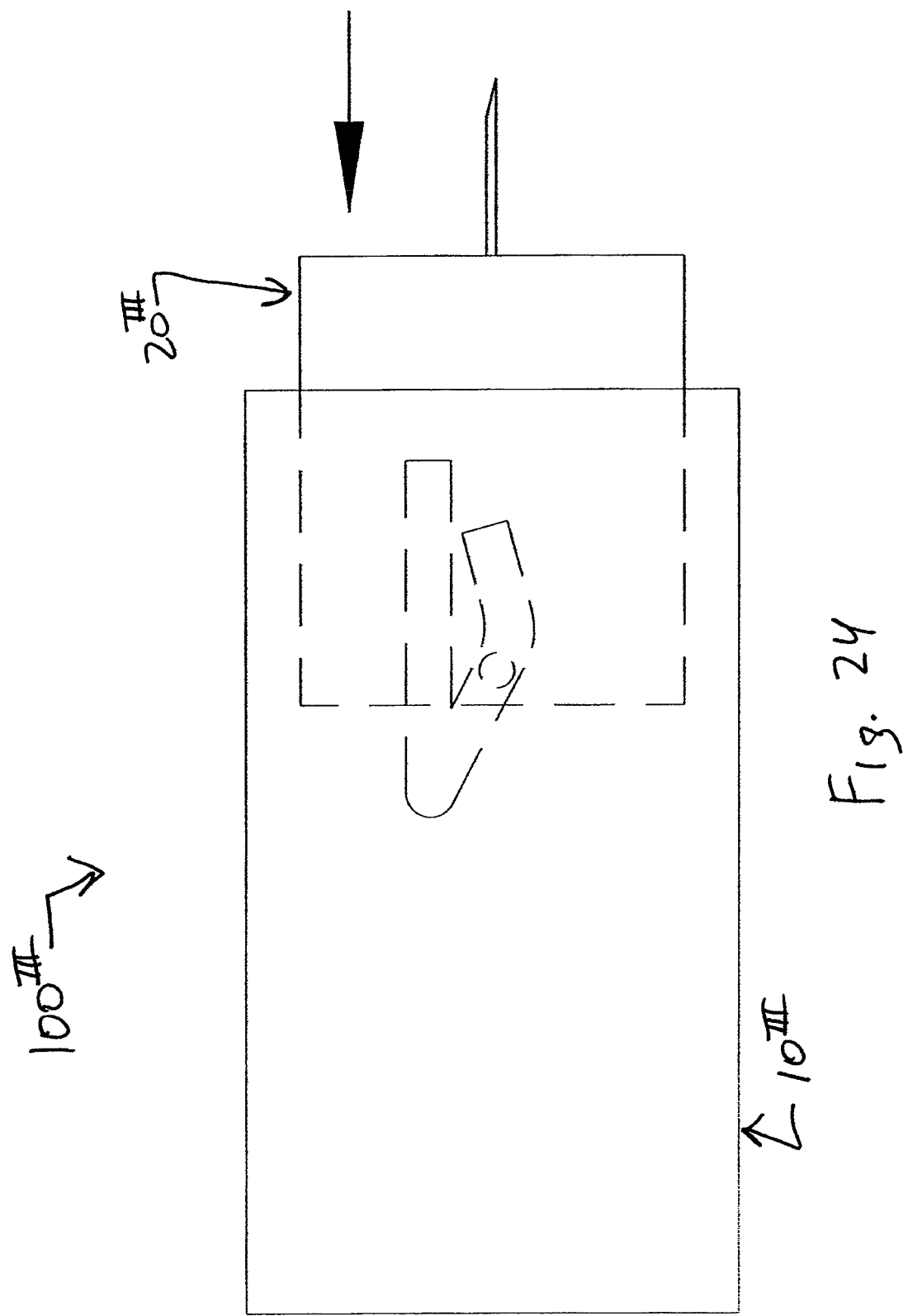
Figure 25:
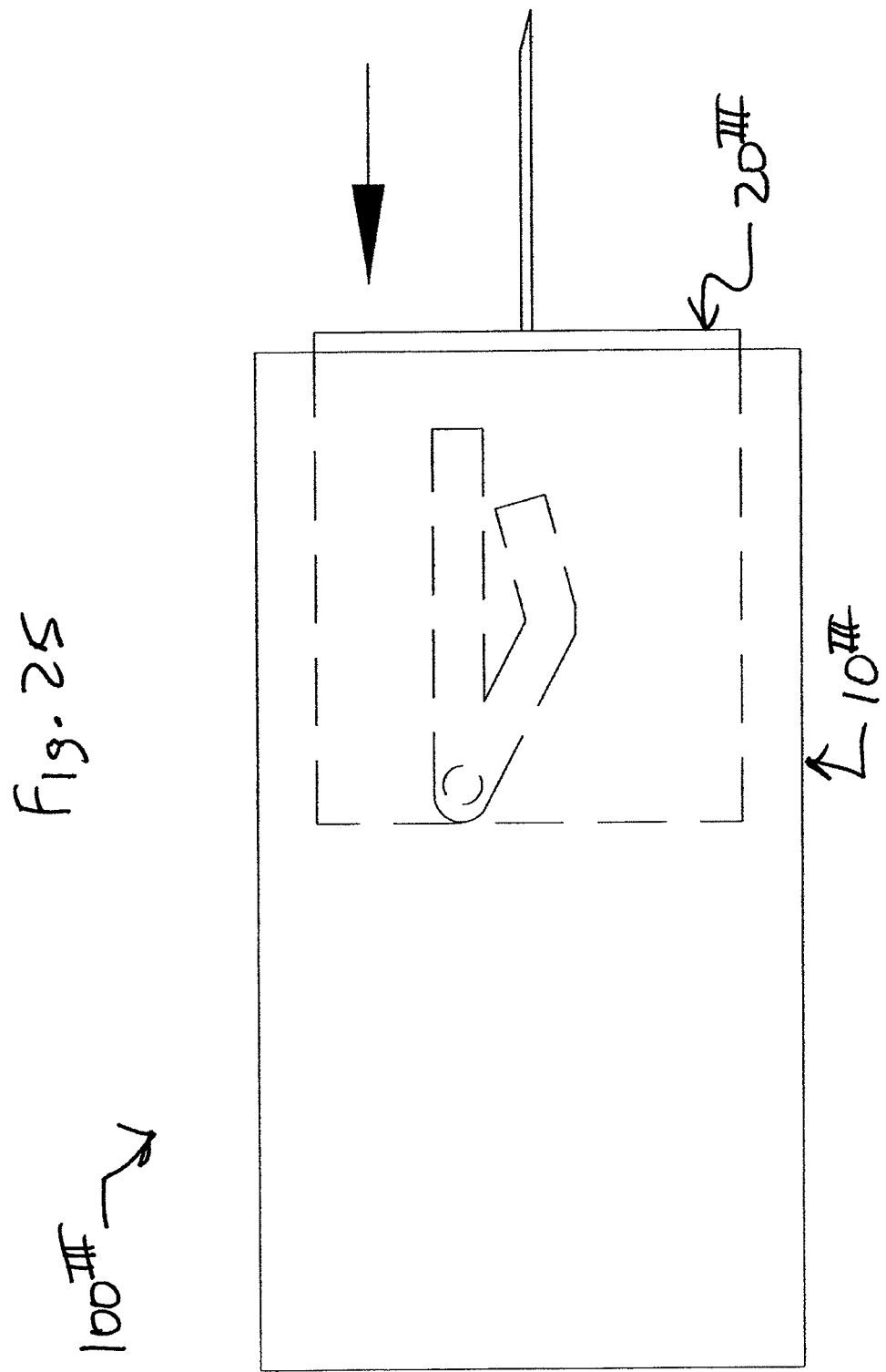
Figure 26:
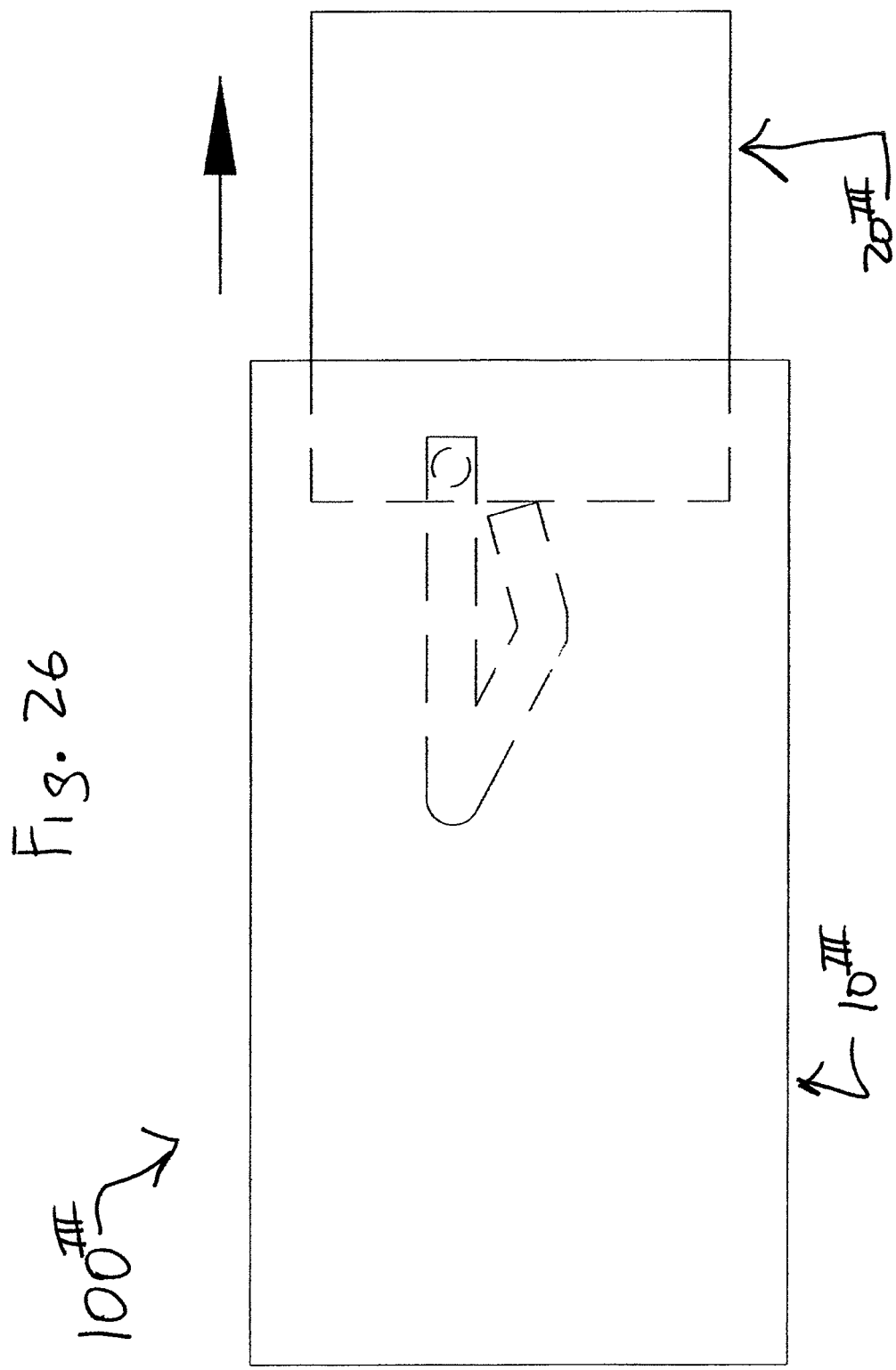

As is evident from FIGS. 23-26, the configuration of each guiding recess GR' is that they each guide or guidingly engage with one of the guiding projections GP' of the shield $20^{III}$ from the initial or intermediate position shown in FIG. 23, to a partially retracted position shown in FIG. 24, to the fully retracted position shown in FIG. 24, and then to the fully extended or locked post-use position shown in FIG. 26. Thus, when the shield $20^{III}$ moves from the initial or intermediate position shown in FIG. 23 to a partially retracted position shown in FIG. 24, it experiences axial and partial rotation movement in two directions. When the shield $20^{III}$ moves from the position shown in FIG. 24 to position shown in FIG. 25, it experiences axial and partial rotation movement in one direction. When the shield $20^{III}$ moves from the position shown in FIG. 25 to position shown in FIG. 26, it experiences only axial linear movement.

Thus, the non-limiting embodiment of FIGS. 19-26 provides for a safety shield $20^{III}$ that rotates at least partially in opposite directions as it moves from the initial position (see FIG. 23) to the retracted position (see FIG. 25). Additionally or alternatively, the safety shield $20^{III}$ includes at least one projection GP' that extends into a guide recess GR' comprising at least a linear section and a curved section. Additionally or alternatively, the safety shield $20^{III}$ includes at least one projection GP' that extends into a guide recess GR' comprising at least a linear section and an angled section.

Figure 27:
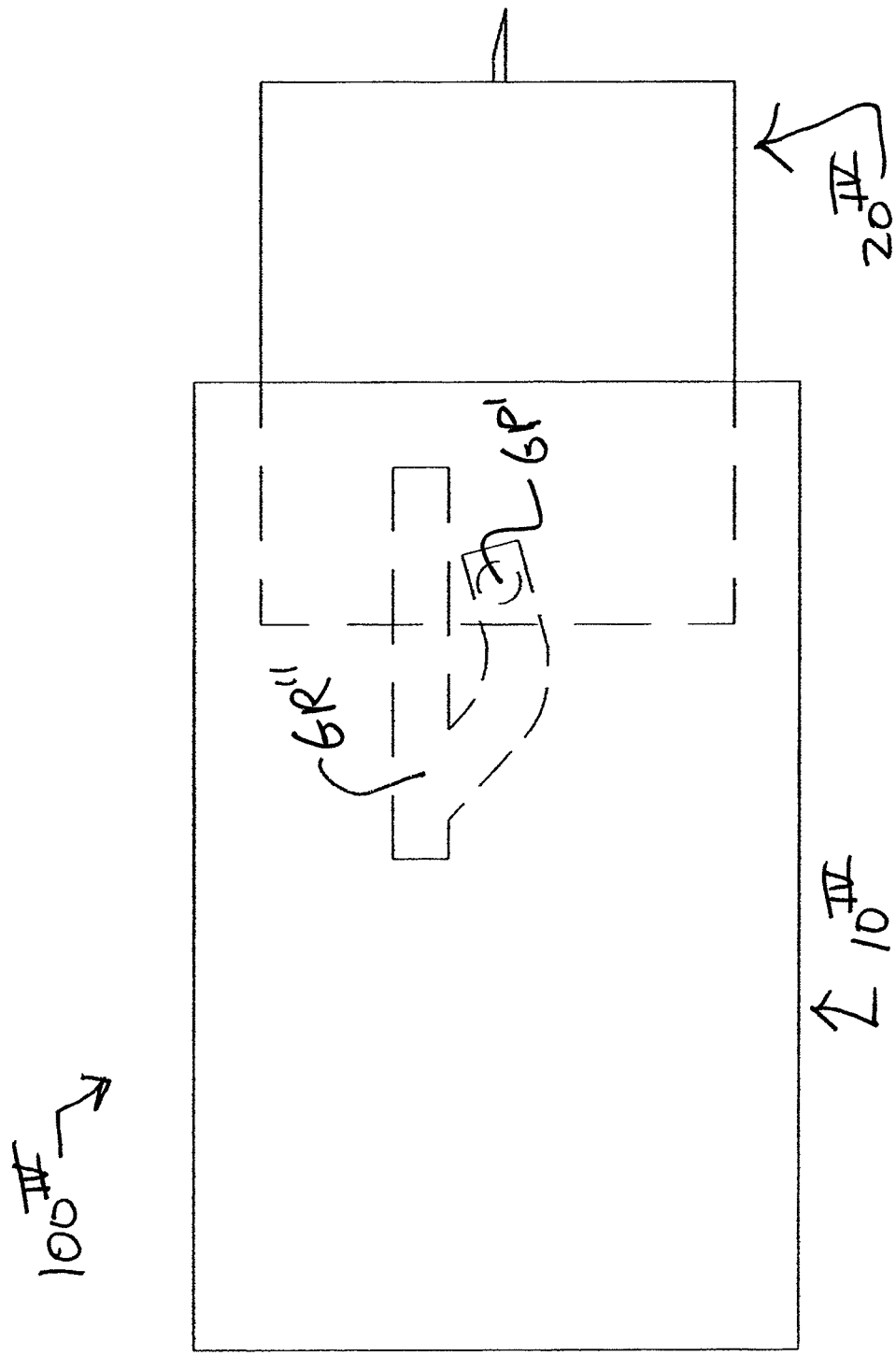
FIG. 27 shows a fifth non-limiting embodiment of the pen needle or needle tip in accordance with the invention.

FIG. 27 shows another non-limiting embodiment of the pen needle or needle tip $100^{IV}$ in accordance with the invention. The needle tip $100^{IV}$ has a rear or distal portion that is removably connected, e.g., threadably connected, to the threaded section 2 of a pen needle injection device 1. More specifically, the needle tip $100^{IV}$ has a body portion $10^{IV}$, e.g., one-piece or integrally formed body, and a safety shield $20^{IV}$, e.g., a one-piece or integrally formed safety shield. In embodiments, a protective cap or cover can be utilized (not shown) so that the needle tip $100^{IV}$ can be safely packaged, shipped and/or installed on the injector 1. Once the needle tip $100^{IV}$ is installed, the protective cap can be removed and even discarded. Similar to that of FIGS. 19-26, the needle shield $20^{IV}$ includes oppositely arranged guiding projections GP' which can deflect inwardly and engage with one or more guiding recesses GR'' arranged on the body $10^{IV}$.

As is evident from FIG. 27, the configuration of each guiding recess GR'' is that they each guide or guidingly engage with one of the guiding projections GP' of the shield $20^{IV}$ from the initial or intermediate position shown in FIG. 27, to a partially retracted position (not shown but similar to that shown in FIG. 24), to the fully retracted position shown (not shown but similar to that in FIG. 24), and then to the fully extended or locked post-use position (not shown but similar to that shown in FIG. 26). Thus, when the shield $20^{IV}$ moves from the initial or intermediate position shown in FIG. 27 to a partially retracted position, it experiences axial and partial rotation movement in two directions. When the shield $20^{IV}$ moves from the retracted position to post-use position, it experiences only axial linear movement.

Thus, the non-limiting embodiment of FIG. 27 provides for a safety shield $20^{IV}$ that rotates at least partially in opposite directions as it moves from the initial position (see FIG. 27) to the retracted position. Additionally or alternatively, the safety shield $20^{IV}$ includes at least one projection GP' that extends into a guide recess GR'' comprising at least a linear section and a curved section.

Figure 28:
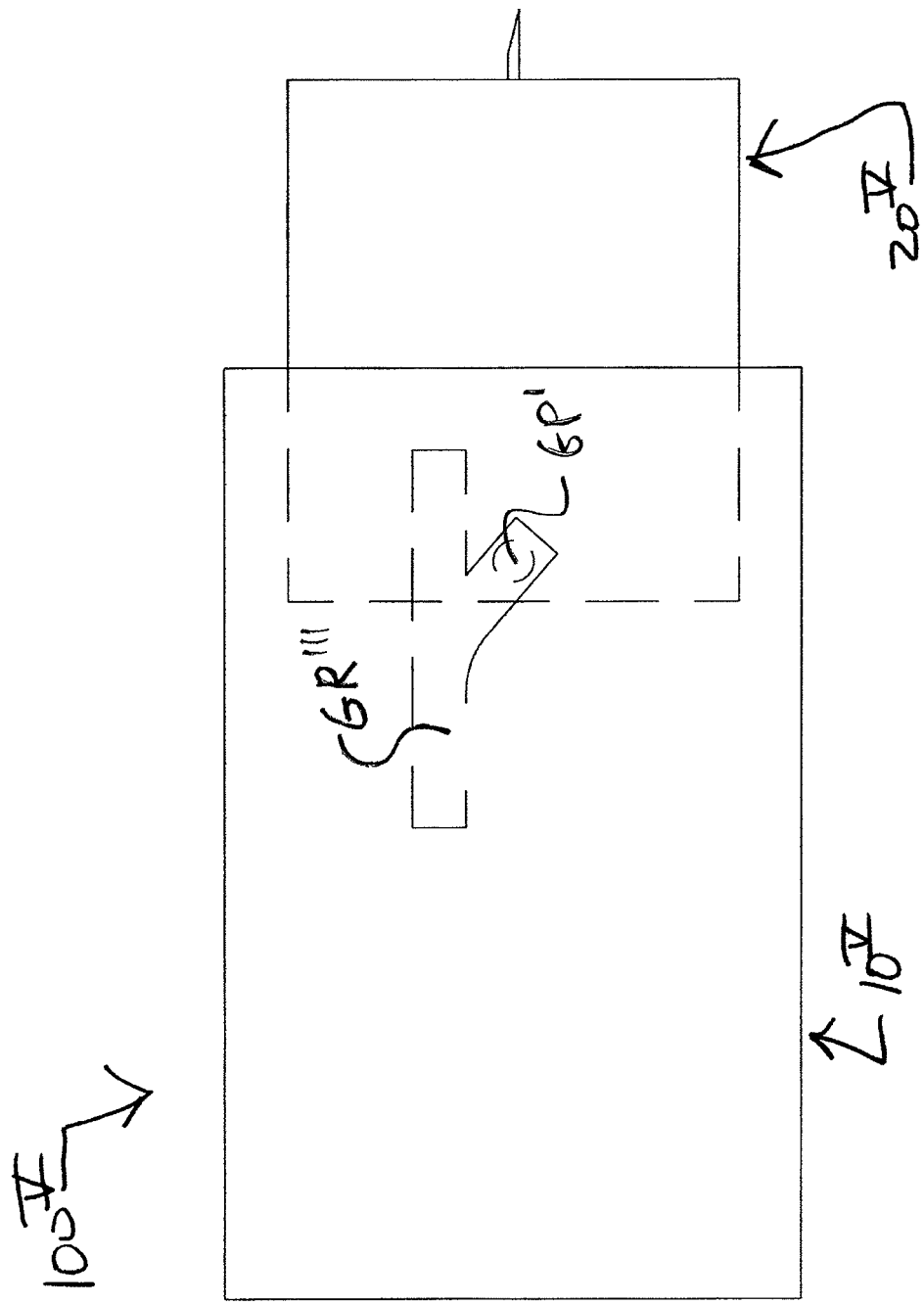
FIG. 28 shows a sixth non-limiting embodiment of the pen needle or needle tip in accordance with the invention.

FIG. 28 shows another non-limiting embodiment of the pen needle or needle tip $100^{V}$ in accordance with the invention. The needle tip $100^{V}$ has a rear or distal portion that is removably connected, e.g., threadably connected, to the threaded section 2 of a pen needle injection device 1. More specifically, the needle tip $100^{V}$ has a body portion $10^{V}$, e.g., one-piece or integrally formed body, and a safety shield $20^{V}$, e.g., a one-piece or integrally formed safety shield. In embodiments, a protective cap or cover can be utilized (not shown) so that the needle tip $100^{V}$ can be safely packaged, shipped and/or installed on the injector 1. Once the needle tip $100^{V}$ is installed, the protective cap can be removed and even discarded. Similar to that of FIG. 27, the needle shield $20^{V}$ includes oppositely arranged guiding projections GP' which can deflect inwardly and engage with one or more guiding recesses GR''' arranged on the body $10^{V}$.

As is evident from FIG. 28, the configuration of each guiding recess GR''' is that they each guide or guidingly engage with one of the guiding projections GP' of the shield $20^{V}$ from the initial or intermediate position shown in FIG. 28, to a partially retracted position (not shown but similar to that shown in FIG. 24), to the fully retracted position shown (not shown but similar to that in FIG. 24), and then to the fully extended or locked post-use position (not shown but similar to that shown in FIG. 26). Thus, when the shield $20^{V}$ moves from the initial or intermediate position shown in FIG. 28 to a partially retracted position, it experiences axial and partial rotation movement in only one direction. When the shield $20^{V}$ moves from the retracted position to post-use position, it experiences only axial linear movement.

Thus, the non-limiting embodiment of FIG. 28 provides for a safety shield $20^{V}$ that rotates at least partially in one direction as it moves from the initial position (see FIG. 28) to the retracted position. Additionally or alternatively, the safety shield $20^{V}$ includes at least one projection GP' that extends into a guide recess GR''' comprising at least two linear sections and can trace at least a partially curved path.

Figure 29:
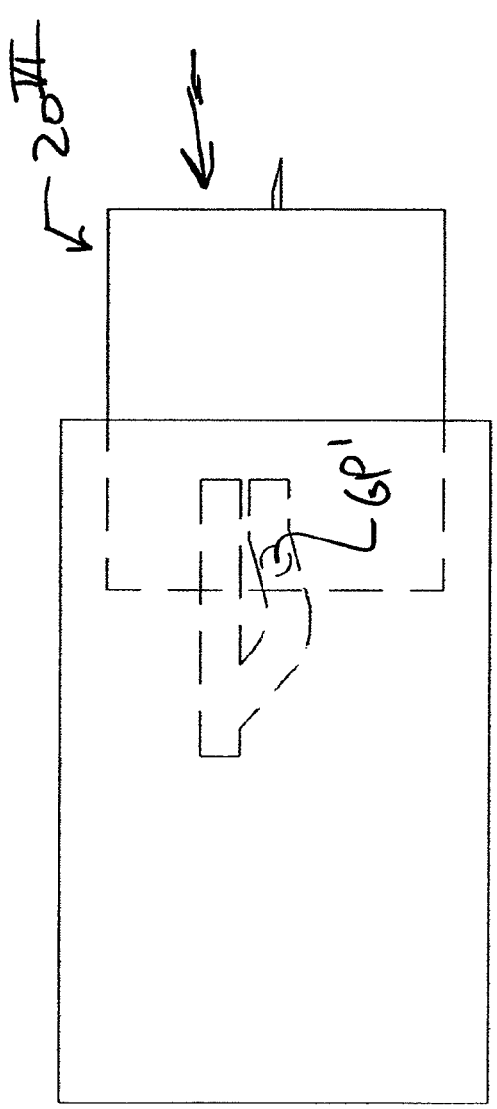
FIGS. 29 and 30 illustrates how a seventh non-limiting embodiment of the pen needle or needle tip can be utilized in accordance with the invention.
Figure 30:
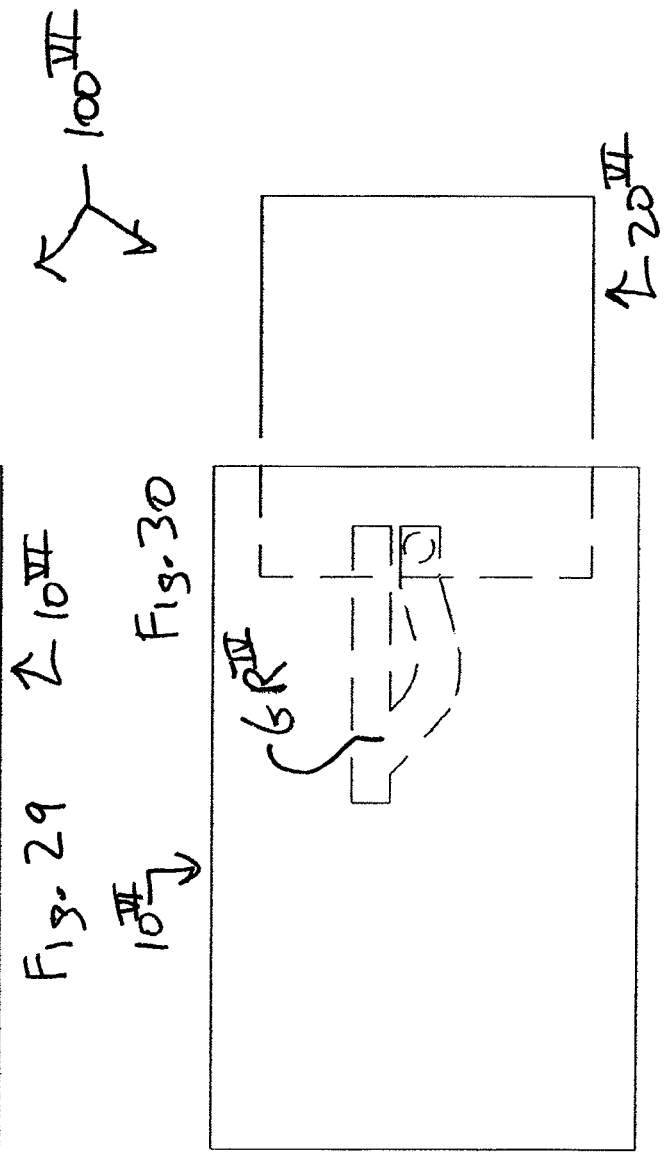

FIGS. 29 and 30 show another non-limiting embodiment of the pen needle or needle tip $100^{VI}$ in accordance with the invention. The needle tip $100^{VI}$ has a rear or distal portion that is removably connected, e.g., threadably connected, to the threaded section 2 of a pen needle injection device 1. More specifically, the needle tip $100^{VI}$ has a body portion $10^{VI}$, e.g., one-piece or integrally formed body, and a safety shield $20^{VI}$, e.g., a one-piece or integrally formed safety shield. In embodiments, a protective cap or cover can be utilized (not shown) so that the needle tip $100^{VI}$ can be safely packaged, shipped and/or installed on the injector 1. Once the needle tip $100^{VI}$ is installed, the protective cap can be removed and even discarded. Similar to that of FIG. 28, the needle shield $20^{VI}$ includes oppositely arranged guiding projections GP' which can deflect inwardly and engage with one or more guiding recesses $GR^{IV}$ arranged on the body $10^{VI}$.

As is evident from FIGS. 29 and 30, the configuration of each guiding recess $GR^{IV}$ is that they each guide or guidingly engage with one of the guiding projections GP' of the shield $20^{VI}$ from the initial position shown in FIG. 30 (which covers or extends out past the needle tip unlike previous embodiments), to a partially retracted position shown in FIG. 29, to the fully retracted position shown (not shown but similar to that in FIG. 24), and then to the fully extended or locked post-use position (not shown but similar to that shown in FIG. 26). Thus, when the shield $20^{VI}$ moves from the initial position shown in FIG. 30 to a partially retracted position, it experiences axial and partial rotation movement in only one direction. When the shield $20^{VI}$ moves axially further back is rotates in another direction. From the retracted position to post-use position, it experiences only axial linear movement.

Thus, the non-limiting embodiment of FIGS. 29 and 30 provides for a safety shield $20^{VI}$ that rotates at least partially in two directions as it moves from the initial position (see FIG. 30) to the retracted position. Additionally or alternatively, the safety shield $20^{VI}$ includes at least one projection GP' that extends into a guide recess $GR^{IV}$ comprising at least two linear sections and at least two curved sections that can trace at least a partially curved path.

FIGS. 31-35 show another non-limiting embodiment of the pen needle or needle tip $100^{VII}$ in accordance with the invention. The needle tip $100^{VII}$ has a rear or distal portion that is removably connected, e.g., threadably connected, to the threaded section 2 of a pen needle injection device 1. More specifically, the needle tip $100^{VII}$ has a body portion $10^{VII}$, e.g., one-piece or integrally formed body, and a safety shield $20^{VII}$, e.g., a one-piece or integrally formed safety shield. In embodiments, a protective cap or cover can be utilized (not shown) so that the needle tip $100^{VII}$ can be safely packaged, shipped and/or installed on the injector 1. Once the needle tip $100^{VII}$ is installed, the protective cap can be removed and even discarded. The needle shield $20^{VII}$ includes oppositely arranged guiding projections GP''' which engage with one or more guiding recesses $GR^V$ arranged on the body $10^{VII}$. Unlike the previous embodiments, however, the needle shield $20^{VII}$ includes an inner circumferential wall ICW and an outer circumferential wall OCW that is axially longer. The wall OCW provides a further way of preventing the user from attempting to reuse the tip $100^{VII}$ after being used once and provides a way to locate the guide recess $GR^V$ on an outer cylindrical surface of the body $10^{VII}$.

Figure 31:
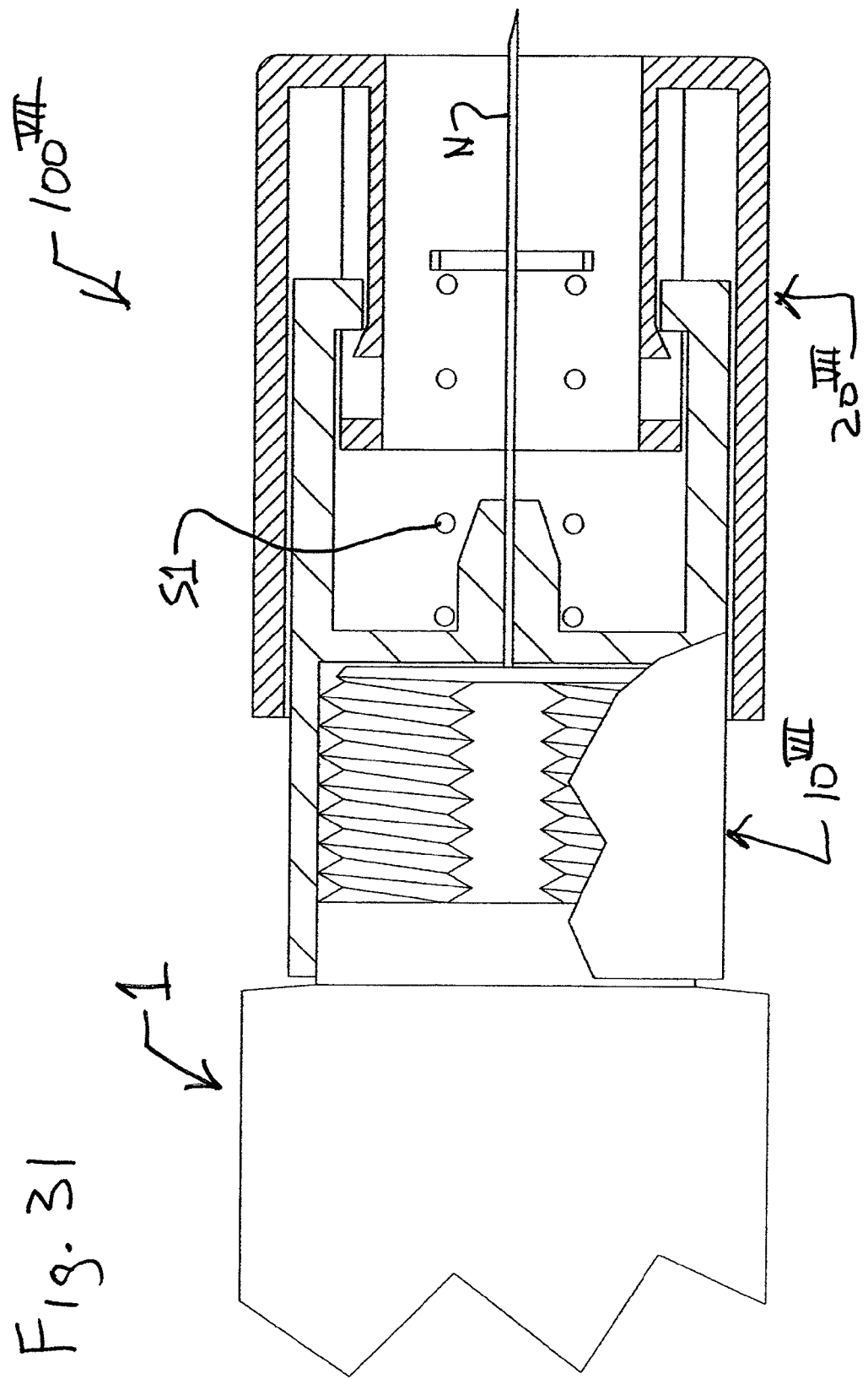
Figure 32:
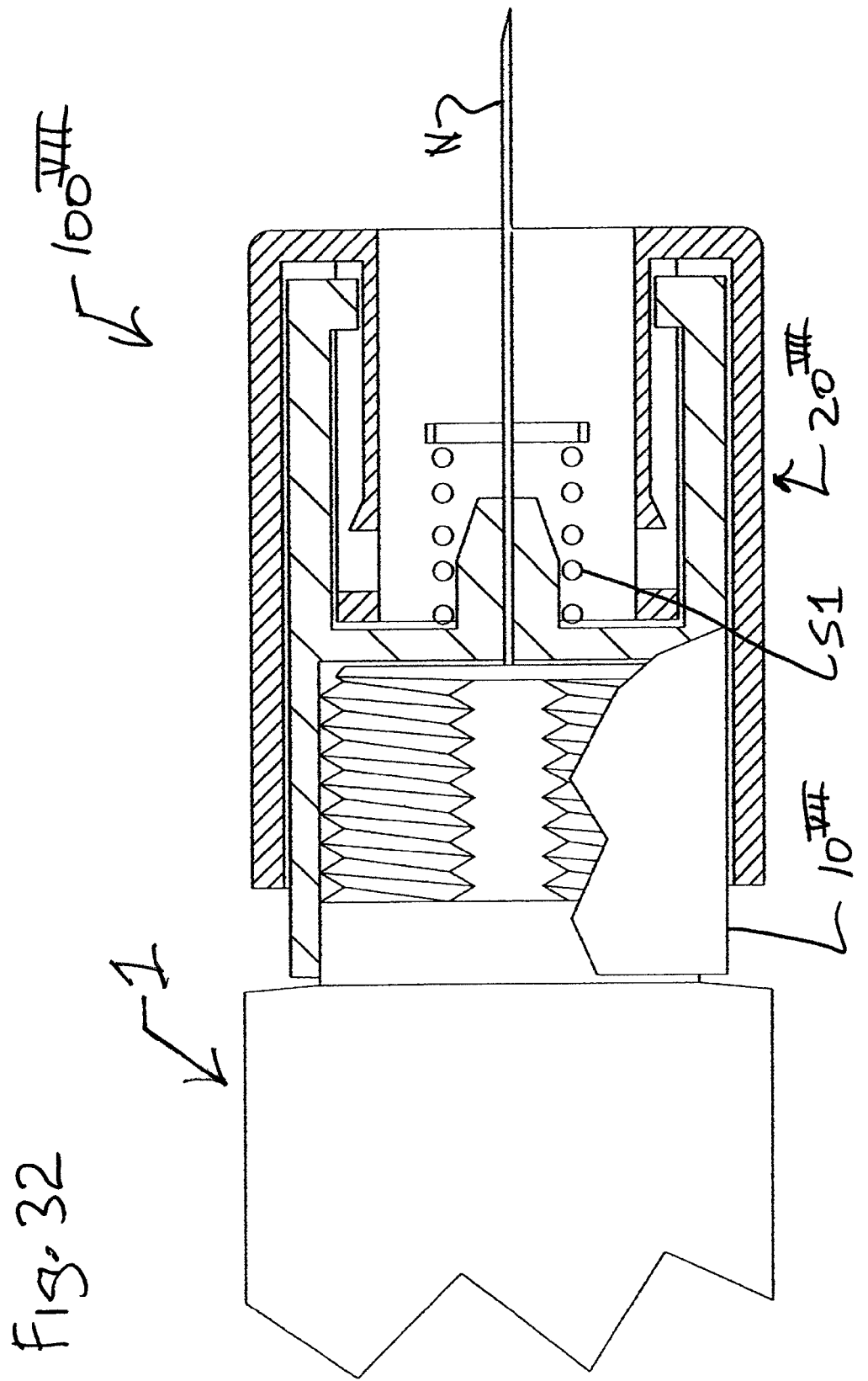
Figure 33:
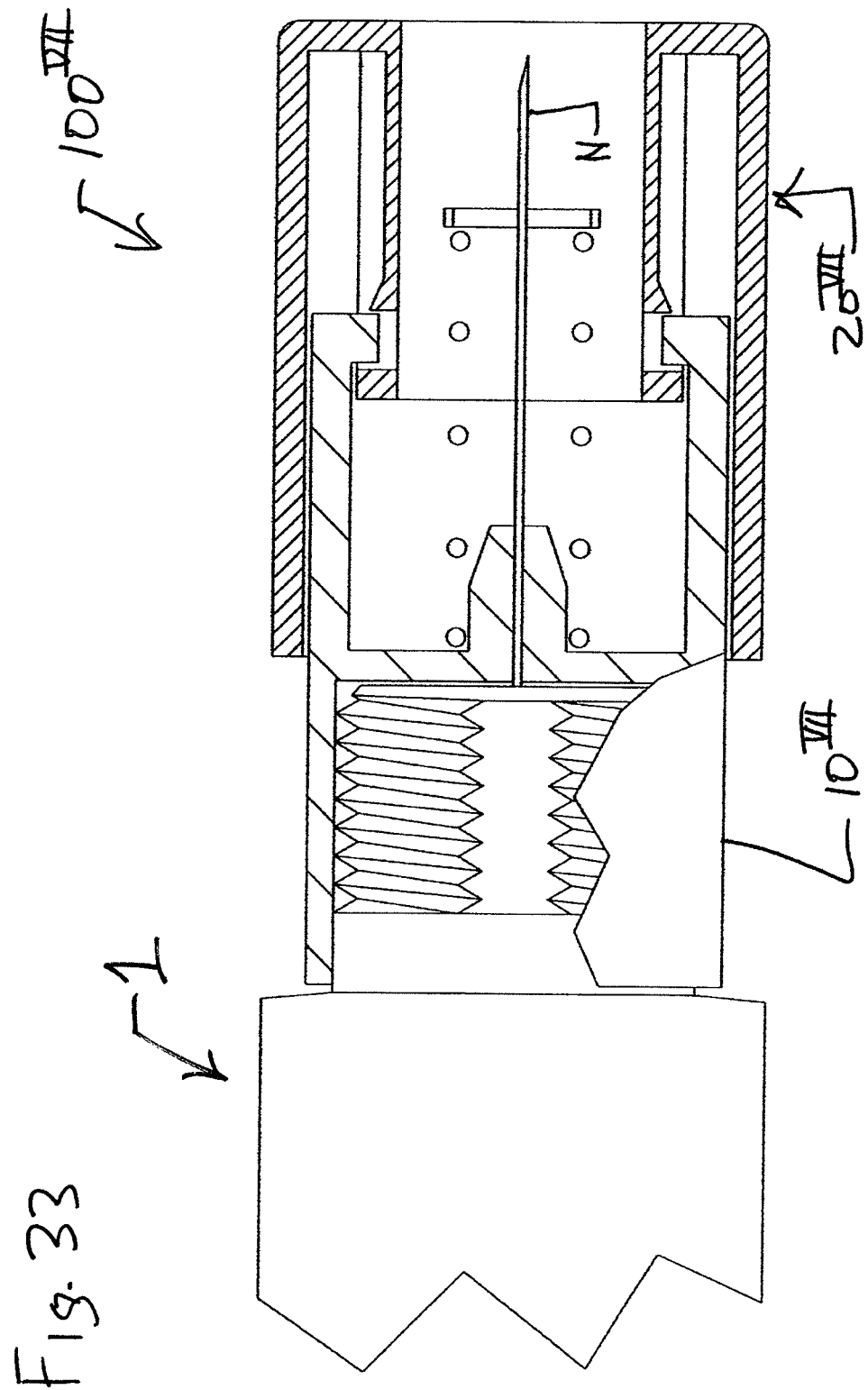
Figure 26:
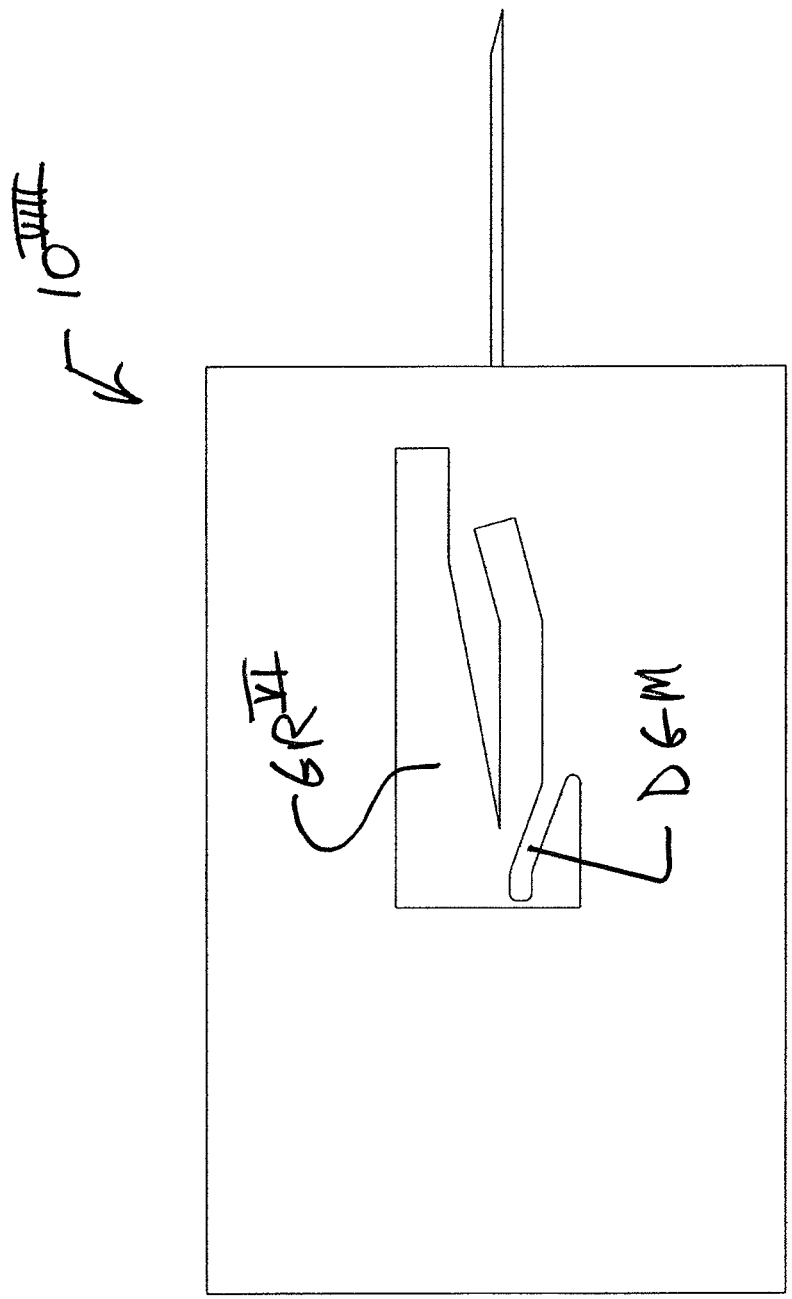

As is evident from FIGS. 31-35, the configuration of each guiding recess $GR^V$ is that they each guide or guidingly engage with one of the guiding projections GP''' of the shield $20^{VII}$ from the initial position shown in FIG. 31 to the fully retracted position shown FIG. 32, and then to the fully extended or locked post-use position shown in FIG. 33. Thus, when the shield $20^{VII}$ moves from the initial position shown in FIG. 31 to a partially retracted position, it experiences axial and partial rotation movement in only one direction. When the shield $20^{VII}$ moves axially further back is rotates in another direction. From the retracted position to post-use position, it experiences only axial linear movement.

Thus, the non-limiting embodiment of FIGS. 31-35 provides for a safety shield $20^{VII}$ that rotates at least partially in two directions as it moves from the initial position (see FIG. 31) to the retracted position (see FIG. 32). Additionally or alternatively, the safety shield $20^{VII}$ includes at least one projection GP''' that extends into a guide recess $GR^V$ comprising three linear sections and at least one curved section that can trace at least a partially curved path.

FIG. 36 shows another non-limiting embodiment of the pen needle or needle tip $100^{VIII}$ in accordance with the invention. The needle tip $100^{VIII}$ has a rear or distal portion that is removably connected, e.g., threadably connected, to the threaded section 2 of a pen needle injection device 1. More specifically, the needle tip $100^{VIII}$ has a body portion $10^{VIII}$, e.g., one-piece or integrally formed body, and a safety shield (not shown, but similar to that shown in FIG. 33). In embodiments, a protective cap or cover can be utilized (not shown) so that the needle tip $100^{VIII}$ can be safely packaged, shipped and/or installed on the injector 1. Once the needle tip $100^{VIII}$ is installed, the protective cap can be removed and even discarded. The needle shield includes oppositely arranged guiding projections which engage with one or more guiding recesses $GR^{VI}$ arranged on the body $10^{VIII}$.

As is evident from FIG. 36, the configuration of each guiding recess $GR^{VI}$ is such that they each guide or guidingly engage with one of the guiding projections of the shield from the initial position shown in FIG. 36 to the fully retracted position, and then to the fully extended or locked post-use position. Thus, when the shield moves from the initial position to a partially retracted position, it experiences axial and partial rotation movement in only one direction. When the shield moves axially further back past the deflectable guide member DGM is rotates slightly in another direction. From the retracted position to post-use position, it experiences both axial and rotational movement. Moreover, the deflectable guide member DGM can be moved by the guide projection to allow the safety shield to reach the fully retracted position and thereafter move back due to its elastic nature—which prevents the guiding projection of the needle shield from moving back into the original position.

Thus, the non-limiting embodiment of FIG. 36 provides for a safety shield that rotates at least partially in two directions as it moves from the initial position to the retracted position. Additionally or alternatively, the safety shield includes at least one projection that extends into a guide recess $GR^{VI}$ comprising at least two linear sections, two angled sections, and/or at least one deflectable guide member DGM.

Figure 38:
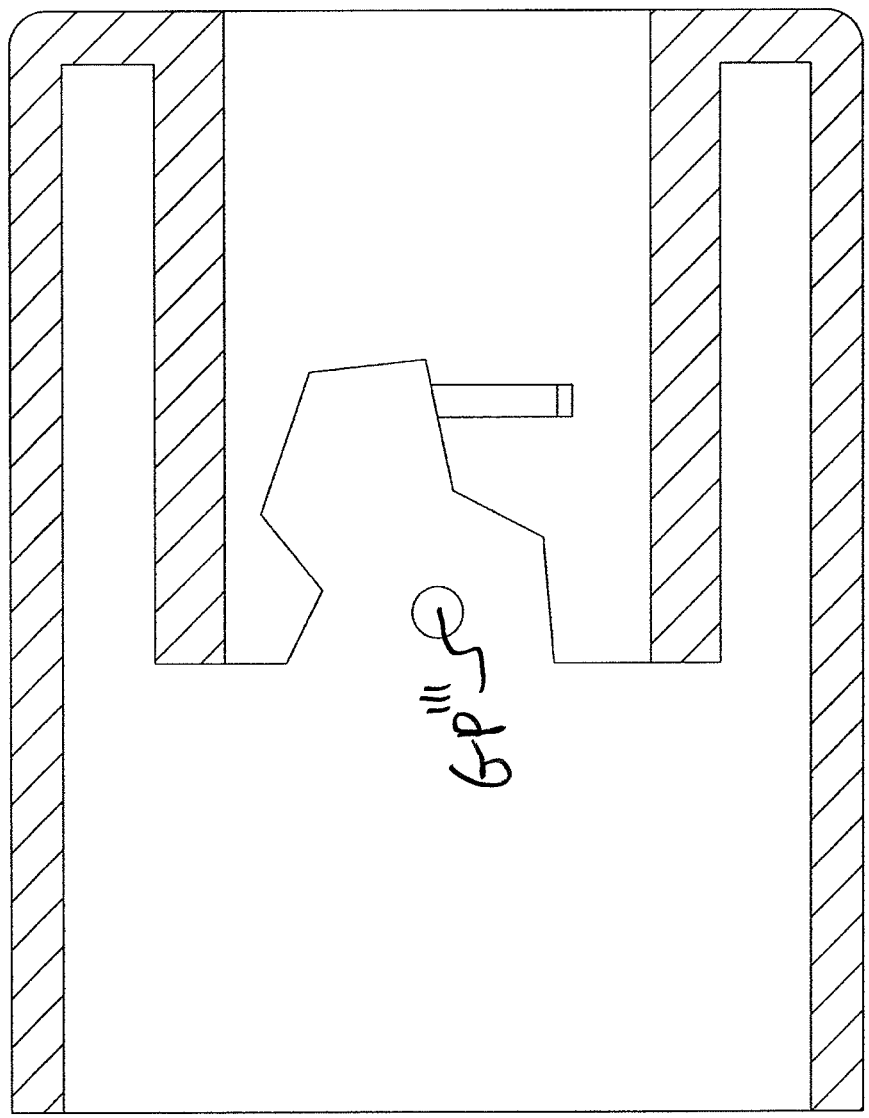
Figure 39:
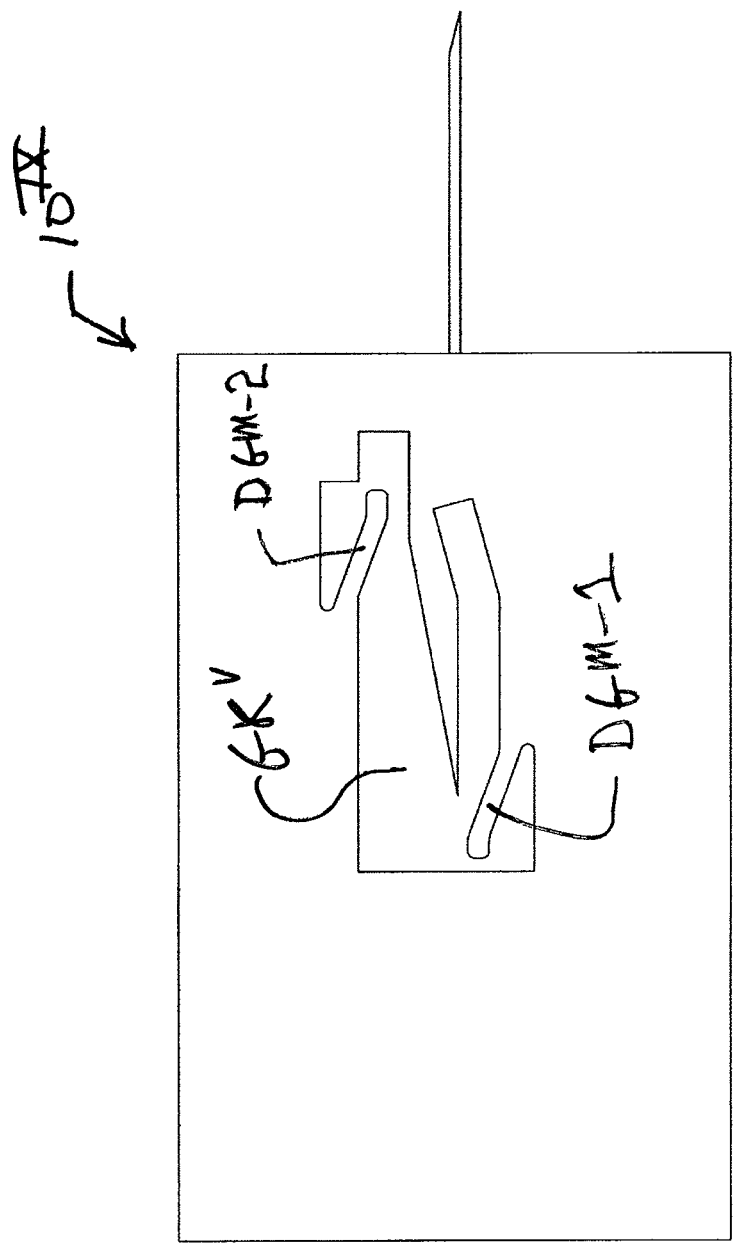

FIGS. 37-39 show another non-limiting embodiment of the pen needle or needle tip $100^{IX}$ in accordance with the invention. The needle tip $100^{IX}$ has a rear or distal portion that is removably connected, e.g., threadably connected, to the threaded section 2 of a pen needle injection device 1. More specifically, the needle tip $100^{IX}$ has a body portion $10^{IX}$, e.g., one-piece or integrally formed body, and a safety shield $20^{IX}$. In embodiments, a protective cap or cover can be utilized (not shown) so that the needle tip $100^{IX}$ can be safely packaged, shipped and/or installed on the injector 1. Once the needle tip $100^{IX}$ is installed, the protective cap can be removed and even discarded. The needle shield includes oppositely arranged guiding projections GP''' which engage with one or more guiding recesses $GR^V$ arranged on the body $10^{IX}$.

As is evident from FIG. 39, the configuration of each guiding recess $GR^V$ is such that they each guide or guidingly engage with one of the guiding projections of the shield $20^{IX}$ from the initial position to the fully retracted position, and then to the fully extended or locked post-use position. Thus, when the shield $20^{IX}$ moves from the initial position to a partially retracted position, it experiences axial and partial rotation movement in only one direction. When the shield moves axially further back past the first deflectable guide member DGM-1 is rotates slightly in another direction. When the shield moves axially forward and past the second deflectable guide member DGM-2 is rotates slightly as well. From the retracted position to post-use position, it experiences both axial and rotational movement. Moreover, the deflectable guide members DGM-1 and DGM-2, which can be moved by the guide projection to allow the safety shield to reach the fully retracted position and to the locked fully extended position respectively, thereafter move back to an original position due to its elastic nature—which prevents the guiding projection(s) GP''' of the needle shield from moving back into the original position and to the retracted position respectively.

Thus, the non-limiting embodiment of FIGS. 37-39 provides for a safety shield $20^{IX}$ that rotates at least partially in two directions as it moves from the initial position to the retracted position. Additionally or alternatively, the safety shield includes at least one projection that extends into a guide recess $GR^V$ comprising at least one linear section, two angled sections, and/or two deflectable guide members DGM-1 and DGM-2. The non-limiting embodiment of FIGS. 37-39 also provides for a safety shield $20^{IX}$ that includes at least one projection GP''' that extends into a guide recess $GR^V$ comprising at least one locking mechanism DGM-2 for retaining the safety shield $20^{IX}$ in the post use locking position.

Figure 40:
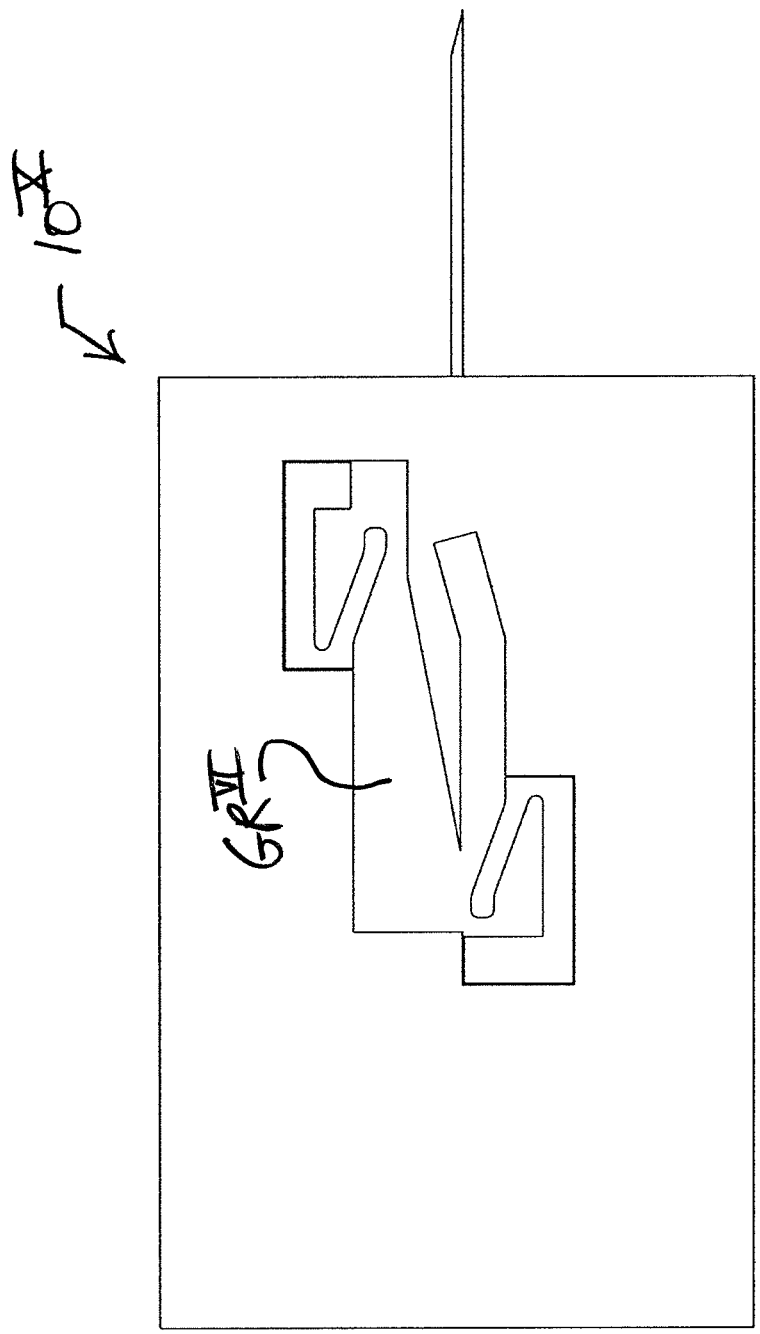
FIGS. 40-41 show an eleventh non-limiting embodiment of the pen needle or needle tip in accordance with the invention.
Figure 41:
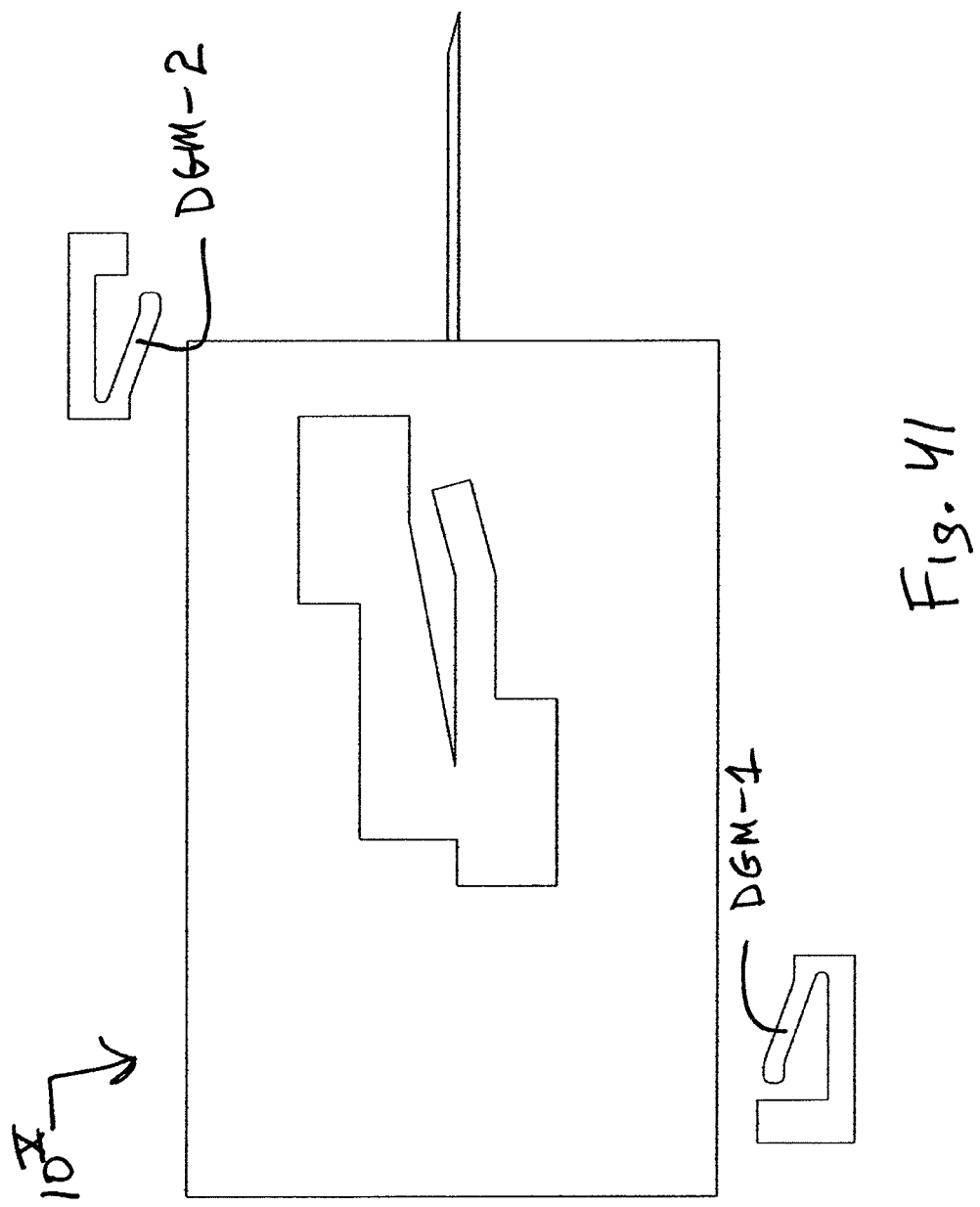

FIGS. 40-41 show another non-limiting embodiment of the pen needle or needle tip $100^X$ in accordance with the invention. The needle tip $100^X$ has a rear or distal portion that is removably connected, e.g., threadably connected, to the threaded section 2 of a pen needle injection device 1. More specifically, the needle tip $100^X$ has a body portion $10^X$, e.g., one-piece or integrally formed body, and a safety shield. In embodiments, a protective cap or cover can be utilized (not shown) so that the needle tip $100^X$ can be safely packaged, shipped and/or installed on the injector 1. Once the needle tip $100^X$ is installed, the protective cap can be removed and even discarded. The needle shield includes oppositely arranged guiding projections which engage with one or more guiding recesses $GR^{VI}$ arranged on the body $10^X$. The arrangement of the one or more guiding recesses $GR^{VI}$ arranged on the body $10^X$ is similar to that of the previous embodiment, except that the portions containing the two deflectable guide members DGM-1 and DGM-2 are separate members which can be inserted into appropriately sized and configured areas of the recess $GR^{VI}$.

Figure 42:
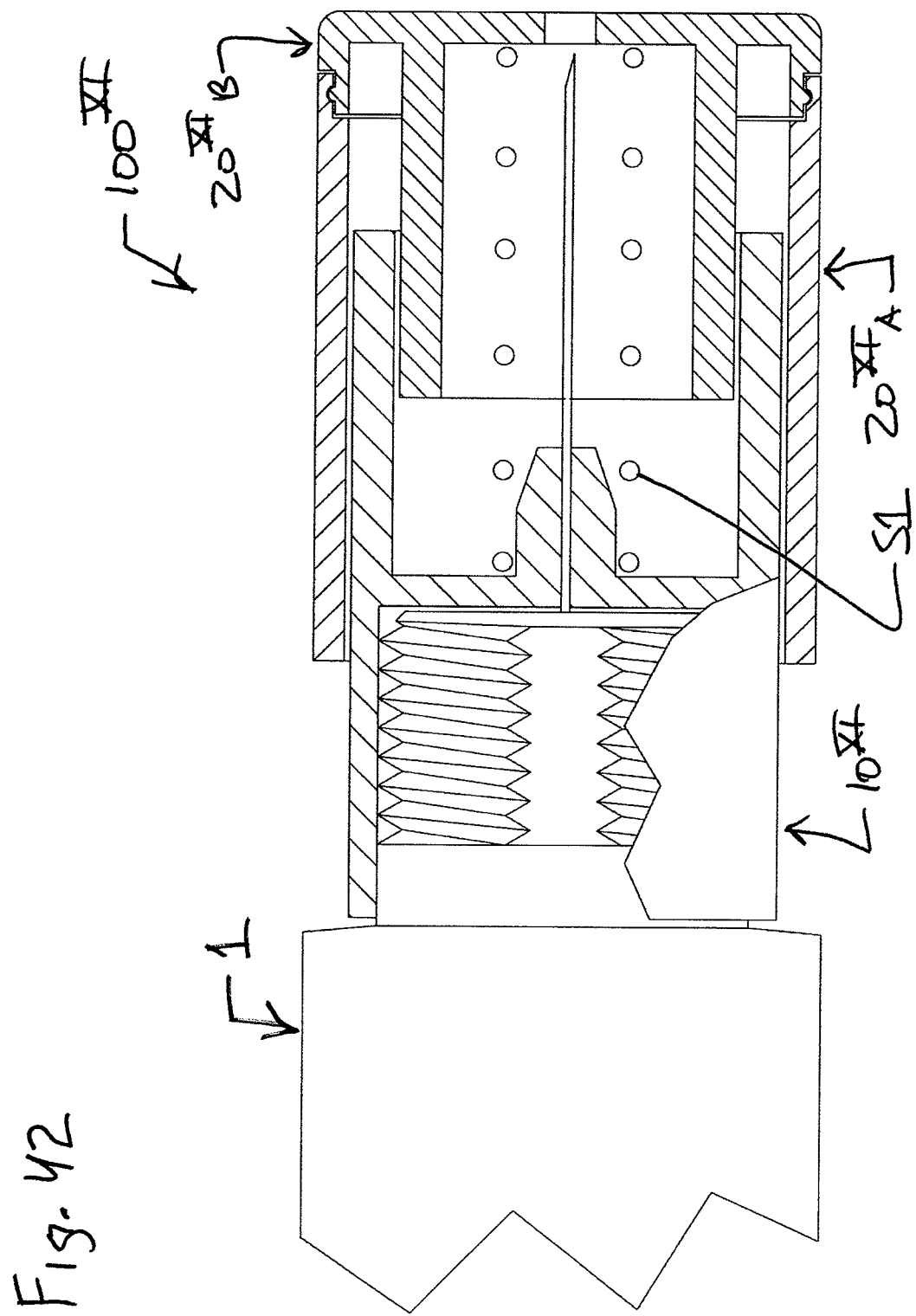
FIGS. 42-43 show a twelfth non-limiting embodiment of the pen needle or needle tip in accordance with the invention.
Figure 43:
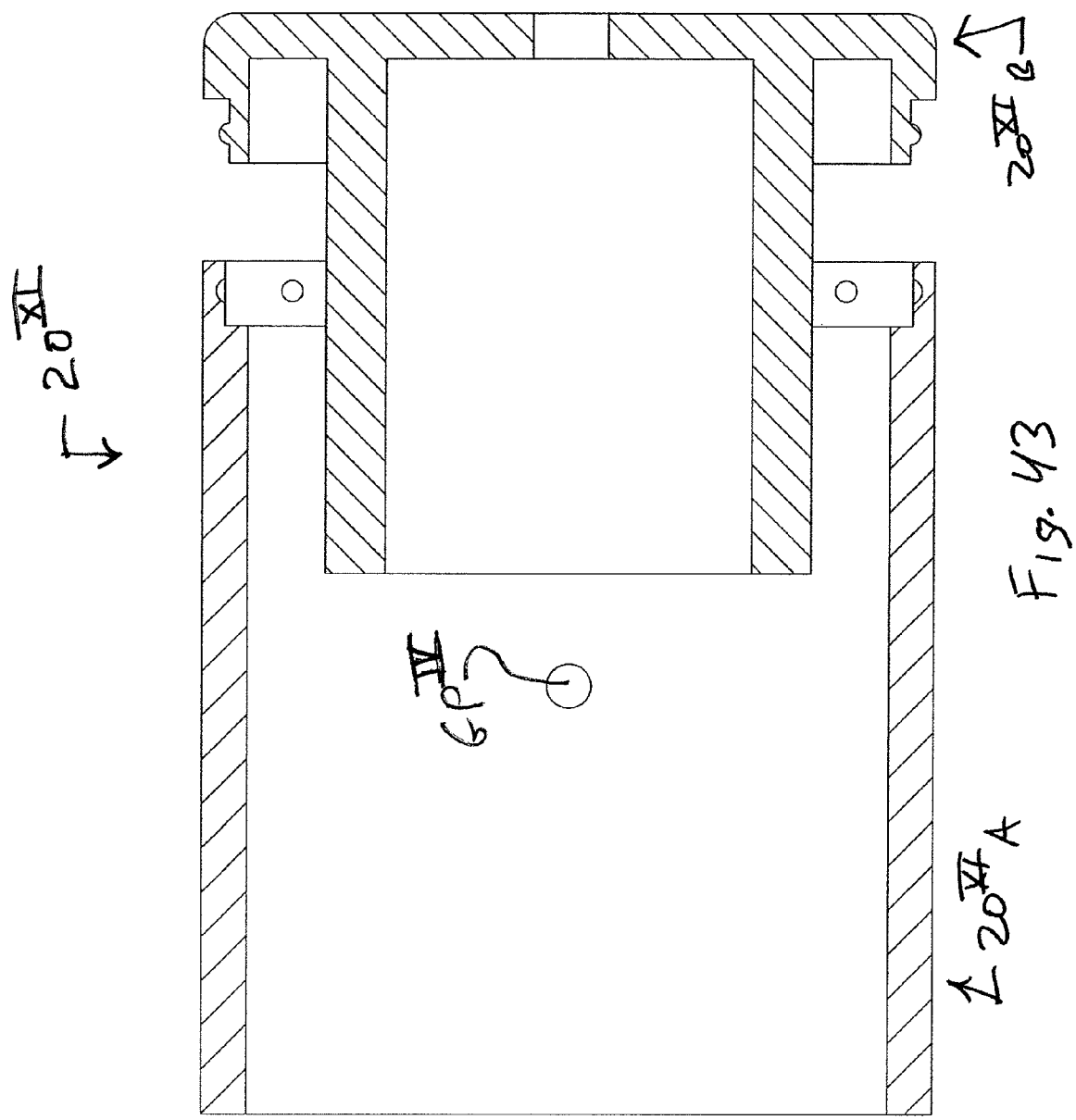

FIGS. 42-43 show another non-limiting embodiment of the pen needle or needle tip $100^{XI}$ in accordance with the invention. The needle tip $100^{XI}$ has a rear or distal portion that is removably connected, e.g., threadably connected, to the threaded section 2 of a pen needle injection device 1. More specifically, the needle tip $100^{XI}$ has a body portion $10^{XI}$, e.g., one-piece or integrally formed body, and a safety shield $20^{XI}$. In embodiments, a protective cap or cover can be utilized (not shown) so that the needle tip $100^{XI}$ can be safely packaged, shipped and/or installed on the injector 1. Once the needle tip $100^{XI}$ is installed, the protective cap can be removed and even discarded. The needle shield $20^{XI}$ includes oppositely arranged guiding projections $GP^{IV}$ which engage with one or more guiding recesses (not shown but similar to those of FIG. 39 or 40) arranged on the body $10^{XI}$. The arrangement of the one or more guiding recesses $GR^{IV}$ arranged on the body $10^{XI}$ is similar to that of the previous embodiment it that it utilizes the two deflectable guide members DGM-1 and DGM-2. With such an arrangement, at least one projection $GP^{IV}$ extends into a guide recess comprising at least one locking mechanism, i.e., one of deflectable guide members DGM-1 and DGM-2 (see FIG. 39 or 40) and one, i.e., deflectable guide member DGM-2, can be utilized to retain the safety shield $20^{XI}$ in the post use locking position. In this embodiment, the inner cylindrical wall does not participate in locking the safety shield $20^{XI}$ in the post use locking position unlike certain previous embodiments. Furthermore, the safety shield $20^{XI}$ can be formed of two main components $20^{XI}$A and $20^{XI}$B attachable via, e.g., a snap connection between one or more projections and one or more recesses as shown in FIG. 43.

FIG. 44 shows another non-limiting embodiment of the pen needle or needle tip $100^{XII}$ in accordance with the invention. The needle tip $100^{XII}$ has a rear or distal portion that is removably connected, e.g., threadably connected, to the threaded section 2 of a pen needle injection device 1. More specifically, the needle tip $100^{XII}$ has a body portion $10^{XII}$, e.g., one-piece or integrally formed body, and a safety shield $20^{XII}$. In embodiments, a protective cap or cover can be utilized (not shown) so that the needle tip $100^{XII}$ can be safely packaged, shipped and/or installed on the injector 1. Once the needle tip $100^{XII}$ is installed, the protective cap can be removed and even discarded. The needle shield $20^{XII}$ includes oppositely arranged guiding projections (not shown but similar to that of the previous embodiment) which engage with one or more guiding recesses (not shown but similar to those of FIG. 35, 36, 39 or 40) arranged on the body $10^{XII}$. The arrangement of the one or more guiding recesses arranged on the body $10^{XII}$ is can function well with the recesses shown in FIGS. 35 and 36, but can also be similar to that of the previous embodiment it that it can utilize the two deflectable guide members DGM-1 and DGM-2 shown in FIGS. 39 and 40. With such an arrangement, at least one projection $GP^{IV}$ extends into a guide recess comprising at least one locking mechanism, i.e., deflectable guide member DGM-2 (see FIG. 39 or 40), and one of these, i.e., deflectable guide member DGM-2, is utilized to retain the safety shield $20^{XII}$ in the post use locking position (creating a double, back-up, or redundant locking system). In this embodiment, the inner cylindrical wall can also participate in locking the safety shield $20^{XII}$ in the post use locking position. Furthermore, the safety shield $20^{XII}$ can be formed of two main components attachable via a snap connection between one or more projections and one or more recesses similar to that shown in FIG. 43.

FIGS. 45 and 46 show another non-limiting embodiment of the pen needle or needle tip $100^{XIII}$ in accordance with the invention. The needle tip $100^{XIII}$ has a rear or distal portion that is removably connected, e.g., threadably connected, to the threaded section 2 of a pen needle injection device 1. More specifically, the needle tip $100^{XIII}$ has a body portion $10^{XIII}$, e.g., one-piece or integrally formed body, and a safety shield $20^{XIII}$, e.g., a one-piece or integrally formed safety shield. In embodiments, a protective cap or cover can be utilized (not shown) so that the needle tip $100^{XIII}$ can be safely packaged, shipped and/or installed on the injector 1. Once the needle tip $100^{XIII}$ is installed, the protective cap can be removed and even discarded. Although similar to that of FIG. 1, this embodiment also utilizes a support ring 30 which functions as a mechanism for preventing a locking of the safety shield $20^{XIII}$ when the shield $20^{XIII}$ in not in the post use locking position, i.e., such as when the shield $20^{XIII}$ is in the initial position. In the position shown in FIG. 45, the ring 30 prevents inward deflection of the tapered projections. As is evident from FIG. 46, during injection the support ring 30 is moved or slid forward relative to its original position (and slight frictional engagement with) inside the safety shield $20^{XIII}$. In this position, it no longer can prevent a locking of the safety shield $20^{XIII}$ so that when the shield $20^{XIII}$ is allowed to move to the extended position under the action of the spring S1, it becomes locked in the post use locking position.

FIG. 47 shows another non-limiting embodiment of the pen needle or needle tip $100^{XIV}$ in accordance with the invention. The needle tip $100^{XIV}$ has a rear or distal portion that is removably connected, e.g., threadably connected, to the threaded section 2 of a pen needle injection device 1. More specifically, the needle tip 100$^{XIV}$ has a body portion 10$^{XIV}$, e.g., one-piece or integrally formed body, and a safety shield 20$^{XIV}$, e.g., a one-piece or integrally formed safety shield. In embodiments, a protective cap or cover can be utilized (not shown) so that the needle tip 100$^{XIV}$ can be safely packaged, shipped and/or installed on the injector 1. Once the needle tip 100$^{XIV}$ is installed, the protective cap can be removed and even discarded. Although similar to that of FIG. 1, this embodiment also utilizes a support ring 30' (like the embodiment of FIG. 45) which functions as a mechanism for preventing a locking of the safety shield 20$^{XIV}$ when the shield 20$^{XIV}$ in not in the post use locking position, i.e., such as when the shield 20$^{XIV}$ is in the initial position. The ring 30' prevents inward deflection of the tapered projections and also, by having a predefined axial length, provides a predetermined depth of penetration. As should be evident from FIG. 47, during injection the support ring 30' is moved or slid forward relative to its original position (and slight frictional engagement with) inside the safety shield 20$^{XIV}$ until in abuts the wall having the needle opening. This limits injection depth of penetration. Although not shown, the tip 100$^{XIV}$ can include indicia (or other indicators such as color of the body or needle shield) informing the user of the depth of penetration provided by the tip. The indicia or indicator feature can be determined by which of a number of different axial length rings are utilized. For example, a red body may provide an indication for one depth of penetration (determined by how much the puncturing end of the needle N projects out past the shin contact surface of the shield) while a blue body may provide an indication for another depth of penetration, and a green one being different from both the red and blue, etc. When the ring 30' is moved, the ring 30' also no longer can prevent a locking of the safety shield 20$^{XIV}$ so that when the shield 20$^{XIV}$ is allowed to move to the extended position under the action of the spring S1, it becomes locked in the post use locking position. As such, this embodiment provides for a mechanism for preventing a locking of the safety shield when the shield in not in the post use locking position and includes a predetermined depth setting mechanism.

FIG. 48 shows another non-limiting embodiment of the pen needle or needle tip 100$^{XV}$ in accordance with the invention. The needle tip 100$^{XV}$ has a rear or distal portion that is removably connected, e.g., threadably connected, to the threaded section 2 of a pen needle injection device 1. More specifically, the needle tip 100$^{XV}$ has a body portion 10$^{XV}$, e.g., one-piece or integrally formed body, and a safety shield 20$^{XV}$, e.g., a one-piece or integrally formed safety shield. In embodiments, a protective cap or cover can be utilized (not shown) so that the needle tip 100$^{XV}$ can be safely packaged, shipped and/or installed on the injector 1. Once the needle tip 100$^{XV}$ is installed, the protective cap can be removed and even discarded. Although similar to that of FIG. 1, this embodiment also utilizes a support ring 30" (like the embodiments of FIG. 45-47) which functions as a mechanism for preventing a locking of the safety shield 20$^{XV}$ when the shield 20$^{XV}$ in not in the post use locking position, i.e., such as when the shield 20$^{XV}$ is in the initial position. The ring 30" prevents inward deflection of the tapered projections and also, by having a predefined axial length, provides a predetermined depth of penetration. Furthermore, the ring projections RP can provide a visual and/or tactile indicator that the tip 100$^{XV}$ has been used. As should be evident from FIG. 48, during injection the support ring 30" is moved or slid forward relative to its original position (and slight frictional engagement with) inside the safety shield 20$^{XV}$ until in abuts the wall having the needle opening. This limits injection depth of penetration. Although not shown, the tip 100$^{XV}$ can include indicia (or other indicators such as color of the body or needle shield) informing the user of the depth of penetration provided by the tip. The indicia or indicator feature can be determined by which of a number of different axial length rings are utilized. For example, a red body may provide an indication for one depth of penetration (determined by how much the puncturing end of the needle N projects out past the shin contact surface of the shield) while a blue body may provide an indication for another depth of penetration, and a green one being different from both the red and blue, etc. When the ring 30" is moved, the ring 30" also no longer can prevent a locking of the safety shield 20$^{XV}$ so that when the shield 20$^{XV}$ is allowed to move to the extended position under the action of the spring S1, it becomes locked in the post use locking position. As such, this embodiment provides for a mechanism for preventing a locking of the safety shield when the shield in not in the post use locking position and includes a predetermined depth setting mechanism, and also provides includes at least one mechanism for providing a visual and/or tactile indication to the user that the needle tip has been used.

Figure 49:
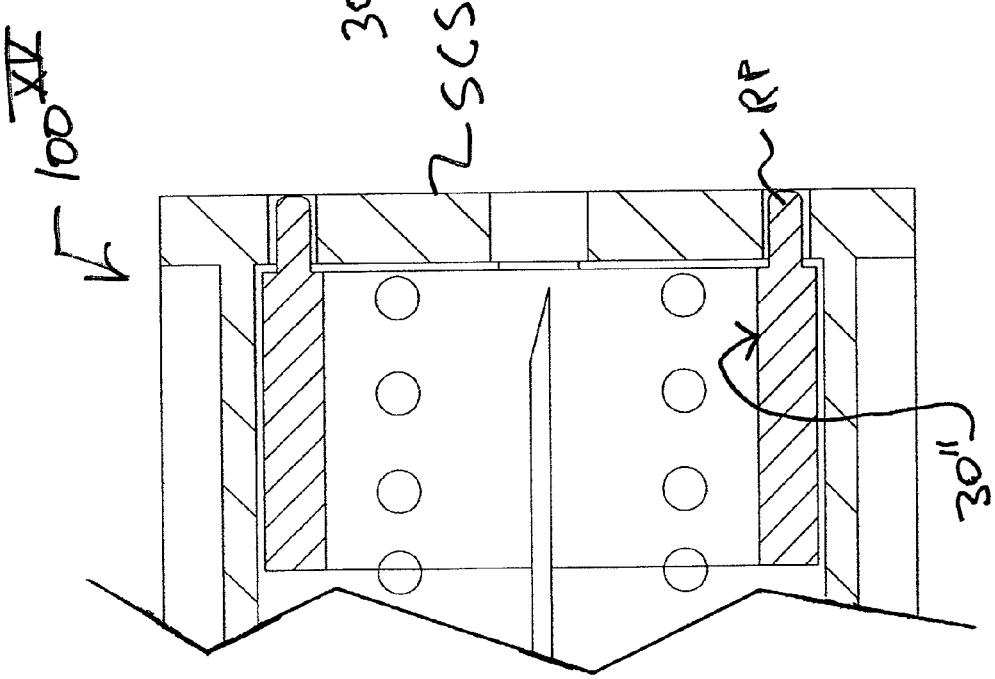

Indeed, in the embodiment of FIG. 49, the ring 30" has ring projections RP which extend to or can be slightly behind the skin contact surface SCS of the shield—thereby providing a visual indicator that the tip 100$^{XV}$ has been used. This can be made more evident, if the one-piece ring 30" is one color, e., red, and the shield is another color, e.g., white. Although not shown, the frictional engagement between ring projections RP and the openings in the wall having the skin contact surface SCS can be significant so that once inserted therein, they cannot be moved back out without easily.

Figure 50:
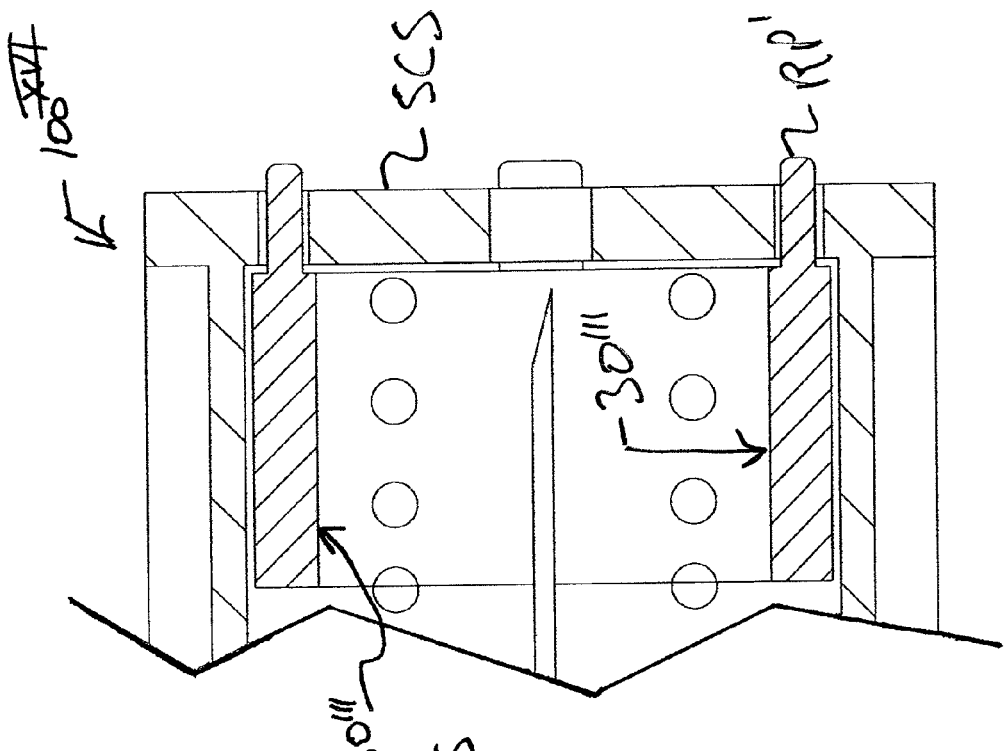
FIG. 50 shows a seventeenth non-limiting embodiment of the pen needle or needle tip in accordance with the invention.

In the embodiment of FIG. 50, the ring 30''' has ring projections RP' which extend out past the skin contact surface SCS of the shield—thereby providing a visual and tactile indicator that the tip 100$^{XVI}$ has been used. This can also be made more evident, if the one-piece ring 30''' is one color, e., red, and the shield is another color, e.g., white. Although not shown, the frictional engagement between ring projections RP and the openings in the wall having the skin contact surface SCS can be significant (or non-releasable) so that once inserted therein, they cannot be moved back out without easily.

In the additional embodiment of FIG. 51, which is a modified version of that of FIG. 1 and can be used on any of the herein disclosed embodiments, the skin contact surface includes a concave surface CS—thereby providing a more comfortable contact surface for the tip 100$^{XVII}$. The needle tip 100$^{XVII}$ has a rear or distal portion that is removably connected, e.g., threadably connected, to the threaded section 2 of a pen needle injection device 1. More specifically, the needle tip 100$^{XVII}$ has a body portion 10$^{XVII}$, e.g., one-piece or integrally formed body, and a safety shield 20$^{XVII}$, e.g., a one-piece or integrally formed safety shield.

In the additional embodiment of FIG. 52, which is a modified version of that of FIG. 1 and can be used on any of the herein disclosed embodiments, the skin contact wall includes self-sealing puncturable member 40—thereby providing a safe covering for the needle N of the tip 100$^{XVIII}$. The needle tip 100$^{XVIII}$ has a rear or distal portion that is removably connected, e.g., threadably connected, to the threaded section 2 of a pen needle injection device 1. More specifically, the needle tip 100$^{XVIII}$ has a body portion 10$^{XVIII}$, e.g., one-piece or integrally formed body, and a safety shield 20$^{XVIII}$, e.g., a one-piece or integrally formed safety shield. This embodiment thus provides for a pierceable member that is pierced during injection and/or a pierceable and resealable member that is pierced during injection.

In the additional embodiment of FIG. 53, which is a modified version of that of FIG. 1 and can be used on any of the herein disclosed embodiments, the body is made as a two-piece arrangement that is, e.g., threadably connected. The needle tip $100^{XIX}$ has a rear or distal portion that is removably connected, e.g., threadably connected, to the threaded section 2 of a pen needle injection device 1. More specifically, the needle tip $100^{XIX}$ has a two-piece body $10^{XIX}$, e.g., both parts $10^{XIX}$A and $10^{XIX}$B can be one-piece or integrally formed members. A safety shield $20^{XIX}$, e.g., a one-piece or integrally formed safety shield, is also utilized. Furthermore, by providing a threaded connection between the body parts, this embodiment thus provides a depth adjustment mechanism DAM for controlling a depth of injection and that is limited at least between two stop or axial positions. In the position shown in FIG. 53, the needle N would provide for one injection depth. However, by unthreading the part $10^{XIX}$B from the part $10^{XIX}$A, the depth of injection would be reduced. These user determined adjustments occur when the depth of penetration is determined by contact between movable stop surface MSS and the set stop surface SSS. Although not shown, indicia can be provided to indicate to the user which depth setting the tip is current set to.

In the additional embodiment of FIG. 54, which is a modified version of that of FIG. 37 and can be used on any of the herein disclosed embodiments, the shield is made as a two-piece arrangement that is, e.g., threadably connected. The needle tip has a rear or distal portion that is removably connected, e.g., threadably connected, to the threaded section 2 of a pen needle injection device 1. More specifically, the needle tip has a two-piece shield $20^{XX}$, e.g., both parts $20^{XX}$A and $20^{XX}$B can be one-piece or integrally formed members. Furthermore, by providing a threaded connection between the shield parts, this embodiment thus provides a depth adjustment mechanism for controlling a depth of injection and that is limited at least between two stop or axial positions. By threading on or unthreading the part $20^{XX}$B from the part $20^{XX}$A, the depth of injection can be changed. Although not shown, indicia can be provided to indicate to the user which depth setting the tip is current set to.

The devices described herein can preferably be single-use and can also utilize one or more features disclosed in prior art documents expressly incorporated by reference in pending U.S. patent application Ser. No. 11/616,195 (Publication No. 2008/0154192). Moreover, the invention specifically contemplates and recognizes using any one or more features or elements of one embodiment on any one or more of the other herein disclosed embodiments. This application and the documents expressly incorporated therein are hereby expressly incorporated by reference in the instant application. Furthermore, one or more of the various parts of each device or embodiment can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF MAIN REFERENCE NUMBERS

Pen needle injection device $100$-$100^{XX}$;
Body $10$-$10^{XX}$;
Safety Shield $20$-$20^{XX}$;
Retaining ring or member 30;
Pierceable and/or resealable member 40;
Spring S1;
Double-ended hollow needle N;
Protective cover PC, PC';
Non-planar or concave surface CS;
Depth Adjustment Mechanism DAM;
Pre-filed syringe 1; and
Threaded section 2.

What is claimed:

1. A needle tip for a pre-loaded injection device comprising:
 a body having a front portion, a back portion configured to be removably connected to the pre-loaded injection device, and a separating wall separating the front and back portions;
 a hollow needle having a first piercing portion projecting back from the separating wall and a second piercing portion projecting forward from the separating wall;
 a safety shield that is axially movable relative to the body between an initial position, a retracted position, and a post use locking position; and
 the safety shield having a first portion extending at least partially into an internal space located within the front portion when the safety shield is in the initial position,
 wherein the safety shield is each of:
  retained in the initial position wherein a puncturing end of the second piercing portion is exposed; and
  prevented from retracting fully into the internal space located within the front portion.

2. The tip of claim 1, further comprising at least one mechanism for providing an indication to the user that the needle tip has been used.

3. The tip of claim 1, wherein the safety shield includes a locking system which is prevented from being contacted by a user's fingers, and moves linearly without also rotating.

4. The tip of claim 1, wherein the safety shield rotates at least partially in opposite directions as it moves from the initial position to the post use locking position.

5. The tip of claim 1, wherein the safety shield rotates at least partially in opposite directions as it moves from the initial position to the retracted position.

6. The tip of claim 1, wherein the safety shield includes at least one projection that extends into a guide recess comprising at least a linear section and a curved section.

7. The tip of claim 1, wherein the safety shield includes at least one projection that extends into a guide recess comprising at least a linear section and an angled section.

8. The tip of claim 1, wherein the safety shield includes at least one projection that extends into a guide recess comprising at least one locking mechanism for retaining the safety shield in the post use locking position.

9. The tip of claim 1, wherein the safety shield includes at least one mechanism for preventing a locking of the safety shield when said shield is not in the post use locking position.

10. A single-use needle tip for a pre-loaded injection device comprising:
- a body having a front portion, a back portion configured to be removably connected to the pre-loaded injection device, and a separating wall separating the front and back portions;
- a hollow needle having a first piercing portion projecting back from the separating wall and a second piercing portion projecting forward from the separating wall;
- a safety shield that is axially movable relative to the body between an initial position, a retracted position, and a post use locking position;
- the safety shield having a first portion extending at least partially into an internal space located within the front portion when the safety shield is in the initial position; and
- a removable cover covering a portion of the safety shield, wherein the safety shield is each of:
    - retained in the initial position wherein a puncturing end of the second piercing portion is exposed; and
    - prevented from retracting fully into the internal space located within the front portion in the retracted position.

11. A single-use needle tip for a pre-loaded injection device comprising:
- a body having a front portion, a back portion configured to be removably connected to the pre-loaded injection device, and a separating wall separating the front and back portions;
- a hollow needle having a first piercing portion projecting back from the separating wall and a second piercing portion projecting forward from the separating wall;
- a safety shield that is axially movable relative to the body between an initial position, a retracted position, and a post use locking position;
- the safety shield having a first portion extending at least partially into an internal space located within the front portion when the safety shield is in the initial position;
- a spring biasing the safety shield toward the initial position; and
- a removable cover covering a portion of the safety shield, wherein the safety shield is each of:
    - retained in the initial position wherein a puncturing end of the second piercing portion is exposed; and
    - prevented, in the retracted position, from retracting fully into the internal space located within the front portion.

* * * * *